US008546334B2

(12) United States Patent
Kohnert et al.

(10) Patent No.: US 8,546,334 B2
(45) Date of Patent: Oct. 1, 2013

(54) DEVICE HAVING OSTEOINDUCTIVE AND OSTEOCONDUCTIVE PROPERTIES

(75) Inventors: Ulrich Kohnert, Habach (DE); Sylke Pohling, Hohenschaftlarn (DE); Klaus Hellerbrand, Geltendorf (DE); Peter Happersberger, Laupheim (DE)

(73) Assignee: Scil Technology GmbH (DE)

( * ) Notice: Subject to any disclaimer, the term of this patent is extended or adjusted under 35 U.S.C. 154(b) by 850 days.

(21) Appl. No.: 10/496,399

(22) PCT Filed: Mar. 27, 2002

(86) PCT No.: PCT/EP02/03463
§ 371 (c)(1),
(2), (4) Date: Feb. 3, 2005

(87) PCT Pub. No.: WO03/043673
PCT Pub. Date: May 30, 2003

(65) Prior Publication Data
US 2006/0088565 A1    Apr. 27, 2006

(30) Foreign Application Priority Data

Nov. 19, 2001  (EP) .................................... 01127573

(51) Int. Cl.
*A61K 38/19*  (2006.01)
*A61K 47/02*  (2006.01)
*C07K 14/51*  (2006.01)
*A61P 19/08*  (2006.01)

(52) U.S. Cl.
USPC ............................ 514/16.7; 514/8.8; 514/769

(58) Field of Classification Search
None
See application file for complete search history.

(56) References Cited

U.S. PATENT DOCUMENTS

| | | |
|---|---|---|
| 4,596,574 A | 6/1986 | Urist |
| 4,877,864 A | 10/1989 | Wang et al. |
| 4,975,526 A | 12/1990 | Kuberasampath et al. |
| 5,011,691 A | 4/1991 | Oppermann et al. |
| 5,013,649 A | 5/1991 | Wang et al. |
| 5,106,748 A | 4/1992 | Wozney et al. |
| 5,108,436 A | 4/1992 | Chu et al. |
| 5,108,922 A | 4/1992 | Wang et al. |
| 5,116,738 A | 5/1992 | Wang et al. |
| 5,141,905 A | 8/1992 | Rosen et al. |
| 5,158,934 A | 10/1992 | Ammann et al. |
| 5,162,114 A | 11/1992 | Kuberasampath et al. |
| 5,166,058 A | 11/1992 | Wang et al. |
| 5,171,574 A | 12/1992 | Kuberasampath et al. |
| 5,177,406 A | 1/1993 | Troxell |
| 5,187,076 A | 2/1993 | Wozney et al. |
| 5,207,710 A | 5/1993 | Chu et al. |
| 5,258,029 A | 11/1993 | Chu et al. |
| 5,258,494 A | 11/1993 | Oppermann et al. |
| 5,266,683 A | 11/1993 | Oppermann et al. |
| 5,290,763 A | 3/1994 | Poser et al. |
| 5,324,819 A | 6/1994 | Oppermann et al. |
| 5,344,654 A | 9/1994 | Rueger et al. |
| 5,354,557 A | 10/1994 | Oppermann et al. |
| 5,366,875 A | 11/1994 | Wozney et al. |
| 5,371,191 A | 12/1994 | Poser et al. |
| 5,385,887 A * | 1/1995 | Yim et al. ........................ 514/12 |
| 5,397,235 A | 3/1995 | Elia |
| 5,409,896 A | 4/1995 | Ammann et al. |
| 5,422,340 A | 6/1995 | Ammann et al. |
| 5,458,653 A | 10/1995 | Davidson |
| 5,459,047 A | 10/1995 | Wozney et al. |
| 5,464,440 A | 11/1995 | Johansson |
| 5,468,845 A | 11/1995 | Oppermann et al. |
| 5,543,394 A | 8/1996 | Wozney et al. |
| 5,563,124 A | 10/1996 | Damien et al. |
| 5,604,204 A | 2/1997 | Ammann et al. |
| 5,607,474 A | 3/1997 | Athanasiou et al. |
| 5,610,021 A | 3/1997 | Rueger et al. |
| 5,618,924 A | 4/1997 | Wang et al. |
| 5,631,142 A | 5/1997 | Wang et al. |
| 5,635,372 A | 6/1997 | Celeste et al. |
| 5,635,373 A | 6/1997 | Wozney et al. |

(Continued)

FOREIGN PATENT DOCUMENTS

DE    196 47 853    5/1998
EP    0 135 083 A2    7/1984

(Continued)

OTHER PUBLICATIONS

Liu et al., The Preliminary Program for the 5th Annual Meeting of the IADR Chinese Division, Jun. 3-5, 2004, meeting abstract.*
Alam et al.; Evaluation of ceramics composed of different hydroxyapatite to tricalcium phosphate ratios as carriers for rhBMP-2; Bionmaterials vol. 22; 2001; p. 1643-1651.
Weng et al., "Bone Regeneration around Implants with Bone Growth Factor rhGDF-5", *J. Dent. Res.*, 2003; 82 (Special Issue b): 377, Abstract # 2943.
Ludwig et al., "GDF-5 coated beta-TCP in sinus augmentation in minipigs", *Int. J. Oral Maxillofac. Surg.*, 2003; 32 (Supplement 1): S55, Abstract O26.9.
Wolfman et al., "Ectopic Induction of Tendon and Ligament in Rats by Growth and Differentiation Factors 5, 6, and 7, Members of the TGF-β Gene Family", *J. Clin. Invest.*, 1997;100(2): 321-330.

(Continued)

*Primary Examiner* — Xiaozhen Xie
(74) *Attorney, Agent, or Firm* — Pillsbury Winthrop Shaw Pittman LLP

(57) ABSTRACT

The present invention relates to a device having osteoinductive and osteoconductive properties in vivo comprising a carrier containing calcium phosphate and an osteoinductive protein, wherein the carrier is homogenously coated with the protein. Moreover, the present invention relates to a method for the production of a device having osteoinductive and osteoconductive properties in vivo. The invention encompasses a pharmaceutical composition comprising the device of the invention or a device which is obtainable by the method of the invention and relates to the use of the device for the preparation of a pharmaceutical composition to be used for bone augmentation, for treating bone defects, for treating degenerative and traumatic disc disease, for treating bone dehiscence or to be used for sinus floor elevation. Finally, the invention relates to a kit comprising the device of the invention or a device which is obtainable by the method of the invention.

12 Claims, 14 Drawing Sheets

(56) References Cited

U.S. PATENT DOCUMENTS

Figure 1:
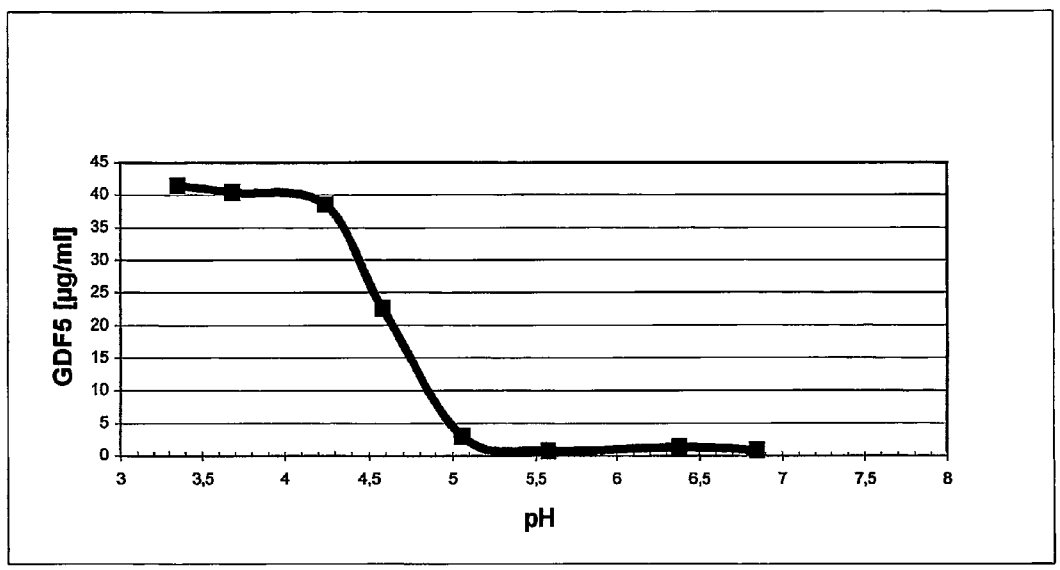

| | | | |
|---|---|---|---|
| 5,650,176 A | 7/1997 | Lee et al. |
| 5,650,276 A | 7/1997 | Smart et al. |
| 5,652,118 A | 7/1997 | Ozkaynak et al. |
| 5,652,337 A | 7/1997 | Oppermann et al. |
| 5,656,593 A | 8/1997 | Kuberasampath et al. |
| 5,658,882 A | 8/1997 | Celeste et al. |
| 5,670,336 A | 9/1997 | Oppermann et al. |
| 5,674,844 A | 10/1997 | Kuberasampath et al. |
| 5,676,976 A | 10/1997 | Lee et al. |
| 5,681,746 A | 10/1997 | Bodner et al. |
| 5,683,461 A | 11/1997 | Lee et al. |
| 5,707,810 A | 1/1998 | Smart et al. |
| 5,714,589 A | 2/1998 | Oppermann et al. |
| 5,728,679 A | 3/1998 | Celeste et al. |
| 5,733,878 A | 3/1998 | Kuberasampath et al. |
| 5,739,107 A | 4/1998 | Cohen et al. |
| 5,741,641 A | 4/1998 | Smart et al. |
| 5,750,651 A | 5/1998 | Oppermann et al. |
| 5,801,014 A | 9/1998 | Lee et al. |
| 5,814,604 A | 9/1998 | Oppermann et al. |
| 5,834,179 A | 11/1998 | Jones et al. |
| 5,849,686 A | 12/1998 | Kuberasampath et al. |
| 5,849,880 A | 12/1998 | Wozney et al. |
| 5,854,071 A | 12/1998 | Oppermann et al. |
| 5,863,758 A | 1/1999 | Oppermann et al. |
| 5,876,452 A | 3/1999 | Athanasiou et al. |
| 5,939,388 A | 8/1999 | Rosen et al. |
| 5,958,441 A | 9/1999 | Oppermann et al. |
| 5,972,884 A | 10/1999 | Cohen et al. |
| 5,984,967 A * | 11/1999 | Zdeblick et al. ........... 623/17.16 |
| 5,994,131 A | 11/1999 | Smart et al. |
| 6,013,517 A | 1/2000 | Respess et al. |
| 6,013,853 A | 1/2000 | Athanasiou et al. |
| 6,022,853 A | 2/2000 | Kuberasampath et al. |
| 6,027,742 A | 2/2000 | Lee et al. |
| 6,027,919 A | 2/2000 | Celeste et al. |
| 6,034,229 A | 3/2000 | Celeste et al. |
| 6,069,295 A | 5/2000 | Leitao |
| 6,071,695 A | 6/2000 | Ozkaynak et al. |
| 6,071,708 A | 6/2000 | Jones et al. |
| 6,077,823 A | 6/2000 | Kuberasampath et al. |
| 6,090,776 A | 7/2000 | Kuberasampath et al. |
| 6,117,456 A | 9/2000 | Lee et al. |
| 6,118,043 A | 9/2000 | Nies et al. ........... 623/16 |
| 6,120,760 A | 9/2000 | Hötten et al. |
| 6,129,928 A | 10/2000 | Sarangapani et al. |
| 6,132,463 A | 10/2000 | Lee et al. |
| 6,136,369 A | 10/2000 | Leitao et al. |
| 6,139,578 A | 10/2000 | Lee et al. |
| 6,143,948 A | 11/2000 | Leitao et al. |
| 6,146,686 A | 11/2000 | Leitao |
| 6,150,328 A | 11/2000 | Wang et al. |
| 6,153,583 A | 11/2000 | Oppermann et al. |
| 6,177,406 B1 | 1/2001 | Wang et al. |
| 6,187,742 B1 | 2/2001 | Wozney et al. |
| 6,194,376 B1 | 2/2001 | Kuberasampath et al. |
| 6,197,550 B1 | 3/2001 | Hötten et al. |
| 6,207,813 B1 | 3/2001 | Wozney et al. |
| 6,211,146 B1 | 4/2001 | Kuberasampath et al. |
| 6,214,368 B1 | 4/2001 | Lee et al. |
| 6,245,889 B1 | 6/2001 | Wang et al. |
| 6,245,896 B1 | 6/2001 | Lee et al. |
| 6,261,322 B1 | 7/2001 | Despres, III et al. |
| 6,261,835 B1 | 7/2001 | Oppermann et al. |
| 6,277,151 B1 | 8/2001 | Lee et al. |
| 6,284,872 B1 | 9/2001 | Celeste et al. |
| 6,287,341 B1 | 9/2001 | Lee et al. |
| 6,288,031 B1 | 9/2001 | Kuberasampath et al. |
| 6,297,213 B1 | 10/2001 | Oppermann et al. |
| 6,328,765 B1 | 12/2001 | Hardwick et al. |
| 6,331,312 B1 | 12/2001 | Lee et al. |
| 6,333,312 B1 | 12/2001 | Kuberasampath et al. |
| 6,344,061 B1 | 2/2002 | Leitao et al. |
| 6,365,150 B1 | 4/2002 | Leboulch et al. |
| 6,395,883 B1 | 5/2002 | Jones et al. |
| 6,399,569 B1 | 6/2002 | Cohen et al. |
| 6,423,544 B1 | 7/2002 | Hardy |
| 6,432,919 B1 | 8/2002 | Wang et al. |
| 6,495,513 B1 | 12/2002 | Rueger et al. |
| 6,506,729 B1 | 1/2003 | Rueger et al. |
| 6,531,445 B1 | 3/2003 | Cohen et al. |
| 6,533,821 B1 | 3/2003 | Lally |
| 6,541,037 B1 | 4/2003 | Lee et al. |
| 6,544,290 B1 | 4/2003 | Lee et al. |
| 6,551,995 B1 | 4/2003 | Oppermann et al. |
| 6,555,107 B2 | 4/2003 | Poeschla et al. |
| 6,565,843 B1 | 5/2003 | Cohen et al. |
| 6,586,388 B2 | 7/2003 | Rueger et al. |
| 6,613,744 B2 | 9/2003 | Wozney et al. |
| 6,696,410 B1 * | 2/2004 | Lee et al. ........... 514/2 |
| 6,730,297 B1 | 5/2004 | Davidson et al. |
| 2001/0016347 A1 | 8/2001 | Poeschla et al. |
| 2002/0009822 A1 | 1/2002 | Park |
| 2002/0016635 A1 | 2/2002 | Despres, III et al. |
| 2002/0022885 A1 * | 2/2002 | Ochi ........... 623/16.11 |
| 2002/0037281 A1 | 3/2002 | Davidson et al. |
| 2002/0048805 A1 | 4/2002 | Johnston et al. |
| 2002/0049159 A1 | 4/2002 | Rueger et al. |
| 2002/0068354 A1 | 6/2002 | Johnston et al. |
| 2002/0082224 A1 | 6/2002 | Jolly et al. |
| 2002/0082679 A1 | 6/2002 | Sirhan et al. |
| 2002/0082694 A1 | 6/2002 | McKay |
| 2002/0136692 A1 | 9/2002 | Haroon et al. |
| 2002/0155137 A1 | 10/2002 | Lee et al. |
| 2002/0155167 A1 | 10/2002 | Lee et al. |
| 2002/0160494 A1 | 10/2002 | Celeste et al. |
| 2002/0165361 A1 | 11/2002 | Lee et al. |
| 2002/0169066 A1 | 11/2002 | Cassidy et al. |
| 2003/0003565 A1 | 1/2003 | Dubensky, Jr. et al. |
| 2003/0009225 A1 | 1/2003 | Khandkar et al. |
| 2003/0032586 A1 | 2/2003 | Rueger et al. |
| 2003/0039636 A1 | 2/2003 | Leboulch et al. |
| 2003/0044596 A1 | 3/2003 | Lazarov et al. |
| 2003/0049328 A1 | 3/2003 | Dalal et al. |
| 2003/0049329 A1 | 3/2003 | Lee et al. |
| 2003/0069401 A1 | 4/2003 | Oppermann et al. |
| 2003/0082232 A1 | 5/2003 | Lee et al. |
| 2003/0104611 A1 | 6/2003 | Johnston et al. |
| 2003/0104993 A1 | 6/2003 | Rueger et al. |
| 2003/0105004 A1 | 6/2003 | Jones et al. |
| 2003/0109445 A1 | 6/2003 | Rueger et al. |
| 2003/0124169 A1 | 7/2003 | Oppermann et al. |
| 2003/0125230 A1 | 7/2003 | Cohen et al. |
| 2003/0180376 A1 | 9/2003 | Dalal et al. |
| 2005/0002907 A1 | 1/2005 | Mitrophanous et al. |

FOREIGN PATENT DOCUMENTS

| | | |
|---|---|---|
| EP | 0 361 896 A2 | 4/1990 |
| EP | 0 411 105 B1 | 6/1995 |
| EP | 0 688 869 A1 | 12/1995 |
| EP | 0 688 869 B1 | 12/1995 |
| EP | 0 362 367 B1 | 2/1996 |
| EP | 0 723 013 A2 | 7/1996 |
| EP | 0 723 013 A3 | 7/1996 |
| EP | 0 723 013 B1 | 7/1996 |
| EP | 0 313 578 B1 | 8/1996 |
| EP | 0 372 031 B1 | 9/1996 |
| EP | 0 625 891 B1 | 1/1997 |
| EP | 0 679 097 B1 | 5/1997 |
| EP | 0 806 212 A1 | 11/1997 |
| EP | 0 429 570 B1 | 1/1998 |
| EP | 0 448 704 B1 | 6/1998 |
| EP | 0 643 767 B1 | 7/1998 |
| EP | 0 584 283 B1 | 12/1999 |
| EP | 0 623 031 B1 | 2/2000 |
| EP | 0 601 106 B1 | 5/2000 |
| EP | 0 601 106 B2 | 5/2000 |
| EP | 0 812 207 B1 | 11/2000 |
| EP | 0 575 555 B1 | 8/2001 |
| EP | 1 221 484 A2 | 7/2002 |
| EP | 1 221 484 A3 | 7/2002 |
| EP | 1 225 225 A2 | 7/2002 |
| EP | 1 225 225 A3 | 7/2002 |
| EP | 0 806 211 B1 | 10/2002 |

| | | |
|---|---|---|
| EP | 1 254 956 A2 | 11/2002 |
| EP | 1 254 956 A3 | 11/2002 |
| EP | 0 714 665 B1 | 1/2003 |
| EP | 0 806 212 B1 | 4/2003 |
| EP | 1 150 726 B1 | 11/2003 |
| EP | 0 936 929 B1 | 6/2004 |
| EP | 1 223 990 B1 | 7/2004 |
| EP | 0 729 325 B1 | 11/2004 |
| JP | 2001-50597 | 4/2001 |
| JP | 2001-511042 | 8/2001 |
| WO | 88/00205 A1 | 1/1988 |
| WO | 90/11366 A1 | 10/1990 |
| WO | 93/05751 A2 | 4/1993 |
| WO | 93/16099 A2 | 8/1993 |
| WO | 93/25246 A1 | 12/1993 |
| WO | 94/15653 | 7/1994 |
| WO | 94/15949 A1 | 7/1994 |
| WO | 95/01760 A2 | 1/1995 |
| WO | 95/01760 A3 | 1/1995 |
| WO | 95/13767 A1 | 5/1995 |
| WO | 95/16035 A2 | 6/1995 |
| WO | 95/16035 A3 | 6/1995 |
| WO | 96/36562 A1 | 11/1996 |
| WO | 97/31661 | 9/1997 |
| WO | WO98/16268 A2 | 4/1998 |
| WO | WO98/16268 A3 | 4/1998 |
| WO | 98/21972 A2 | 5/1998 |
| WO | 98/21972 A2 | 5/1998 |
| WO | 98/21972 A3 | 5/1998 |
| WO | 98/21972 A3 | 5/1998 |
| WO | 98/33514 A1 | 8/1998 |
| WO | 98/34655 | 8/1998 |
| WO | 98/40113 A1 | 9/1998 |
| WO | 98/51354 | 11/1998 |
| WO | 99/11202 A1 | 3/1999 |
| WO | 99/58167 A1 | 11/1999 |
| WO | 00/45870 A1 | 8/2000 |
| WO | 00/45871 A1 | 8/2000 |
| WO | 00/72775 | 12/2000 |
| WO | 00/72775 A1 | 12/2000 |
| WO | 00/72776 A1 | 12/2000 |
| WO | 00/72777 A1 | 12/2000 |
| WO | WO 01/08715 A1 * | 2/2001 |
| WO | 01/28602 A1 | 4/2001 |
| WO | 01/28603 A1 | 4/2001 |
| WO | 01/28605 A1 | 4/2001 |
| WO | 91/11148 A1 | 8/2001 |
| WO | 0197679 A2 | 12/2001 |
| WO | 02/070029 A2 | 9/2002 |
| WO | 02/070029 A3 | 9/2002 |
| WO | 02/083188 A2 | 10/2002 |
| WO | 03/003937 A1 | 1/2003 |
| WO | 03/003939 A1 | 1/2003 |

OTHER PUBLICATIONS

GenBank Accession No. NP_00548, (GI:4503969). Growth diffrentiation factor 4 preprotein; cartilage-derived morphogenic protein-1 [*Homo sapiens*]. Last modified Dec. 20, 2003.
GenBank Accession No. P43026 (GI:20141384). Growth/differentiation factor 5 precursor (GDF-5); cartilage-derived morphogenic protein 1 (CDMP-1). Last modified Jun. 15, 2004.
GenBank Accession No. JC2347 (GI:631181). Growth/differentiation factor 5-human. Last modified Mar. 17, 2000.
GenBank Accession No. CAA56874 (GI:671525). Gdf5 [*Homo sapiens*]. Last modified Feb. 24, 1995.
GenBank Accession No. AAH32495 (GI:22749747). GDF5 protein [*Homo sapiens*]. Last modified Oct. 7, 2003.
GenBank Accession No. CAB89416 (GI:7671666). Growth differentiation factor 5; cartilage-derived morphogenic protein-1 [*Homo sapiens*]. Last modified Apr. 11, 2001.
Ripamonti, U., et al., Induction of Bone Formation by Recombinant Human Osteogenic Protein-1 and Sintered Porous Hydroxyapatite in Adult Primates, *Plast. Reconstr. Surg.* 107:977-988 (2001).
Celeste, A.J., et al., Identification of Transforming Growth Factor Beta Family Members Present in Bone-Inductive Protein Purified From Bovine Bone, Proc. Natl. Acad. Sci. U.S.A, 87(24):9843-9847 (1990).
Chang, S.C., et al., Cartilage-Derived Morphogenetic Proteins. New Members of the Transforming Growth Factor-Beta Superfamily Predominantly Expressed in Long Bones During Human Embryonic Development, J. Biol. Chem. 269(45):28227-2823 (1994).
EMEA. ICH Topic Q 3 C—Impurities: Residual Solvents. 1-19. 1997. Ref Type: Generic.
Friess,W., et al., Bone Regeneration With Recombinant Human Bone Morphogenetic Protein-2 (Rhbmp-2) Using Absorbable Collagen Sponges (ACS): Influence of Processing on ACS Characteristics and Formulation, Pharm. Dev. Technol. 4(3):387-96 (1999).
Gao,T., et al., Composites of Bone Morphogenetic Protein (BMP) and Type IV Collagen, Coral-Derived Coral Hydroxyapatite, and Tricalcium Phosphate Ceramics, Int. Orthop., 20(5):321-325 (1996).
Gombotz,W.R., et al., Stability, Characterization, Formulation, and Delivery System Development for Transforming Growth Factor-Beta 1. In Formulation, Characterization, and Stability of Protein Drugs New York and London, 1996; vol. 9, 219-45.
Griffith,D.L., et al., Three-Dimensional Structure of Recombinant Human Osteogenic Protein 1: Structural Paradigm for the Transforming Growth Factor Beta Superfamily, Proc Natl Acad Sci U.S.A., 93(2):878-883 (1996).
Hotten,G., et al., Cloning and Expression of Recombinant Human Growth/Differentiation Factor 5, Biochem. Biophys. Res. Commun., 204(2):646-652 (1994).
Hotz,G., et al., Bone Substitute With Osteoinductive Biomaterials—Current and Future Clinical Applications, Int. J. Oral Maxillofac. Surg., 23(6 Pt 2):413-417 (1994).
Katagiri,T., et al., The Non-Osteogenic Mouse Pluripotent Cell Line, C3H10T1/2, Is Induced to Differentiate Into Osteoblastic Cells by Recombinant Human Bone Morphogenetic Protein-2., Biochem. Biophys. Res. Commun., 172(1):295-299 (1990).
Lind, M., et al., Transforming Growth Factor-Beta 1 Enhances Bone Healing to Unloaded Tricalcium Phosphate Coated Implants: An Experimental Study in Dogs, J. Orthop. Res., 14(3):343-350 (1996).
Lind,M., Growth Factors: Possible New Clinical Tools. A Review, Acta. Orthop. Scand., 67(4):407-17 (1996).
Nishitoh, H., et al., Identification of Type I and Type II Serine/Threonine Kinase Receptors for Growth/Differentiation Factor-5, J. Biol. Chem., 271(35):21345-21352 (1996).
Ozkaynak, E., et al., OP-1 cDNA Encodes an Osteogenic Protein in the TGF-Beta Family, The Embo. J., 9(7):2085-2093 (1990).
Scheufler, C., et al., Crystal Structure of Human Bone Morphogenetib Protein-2 At 2.7 A Resolution, J. Mol. Biol., 287(1):103-115 (1999).
Schmitt, J., et al., Bone Morphogenetic Proteins: An Update on Basic Biology and Clinical Relevance, J. Orthop. Res., 17:269-278 (1999).
Spiro, R.C., et al., Spinal Fusion With Recombinant Human Growth and Differentiation Factor-5 Combined With a Mineralized Collagen Matrix, The Anatomical Record, 263:388-395 (2001).
Storm, E.E., et al., GDF5 Coordinates Bone and Joint Formation During Digit Development, Dev Biol, 209 (1), 11-27 (1999).
Terheyden, H., et al., Recombinant Human Osteogenic Protein 1 in the Rat Mandibular Augmentation Model: Differences in Morphology of the Newly Formed Bone Are Dependent on the Type of Carrier, Mund Kiefer Gesichtschir., 1:272-275.(1997).
Wozney, J.M., et al., Bone Morphogenetic Protein and Bone Morphogenetic Protein Gene Family in Bone Formation and Repair, Clin. Orthop, 346:26-37 (1998).
Wozney, J.M., et al., Novel Regulators of Bone Formation: Molecular Clones and Activities. Science, 242(4885):1528-1534 (1988).
Baldwin, R.L., et al., How Hofmeister Ion Interactions Affect Protein Stability, *Biophysical Journal*, 71:2056-2063 (1996).
US 5,182,365, 01/1993, Oppermann et al. (withdrawn)

* cited by examiner

SEQUENCE LISTING

```
<160> NUMBER OF SEQ ID NOS: 3

<210> SEQ ID NO 1
<211> LENGTH: 396
<212> TYPE: PRT
<213> ORGANISM: Homo Sapiens

<400> SEQUENCE: 1

Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
```

```
                     115                 120                 125
Thr Arg Arg Phe Phe Phe Asn Leu Ser Ser Ile Pro Thr Glu Glu Phe
130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
    210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
        275                 280                 285

Arg Lys Arg Leu Lys Ser Ser Cys Lys Arg His Pro Leu Tyr Val Asp
    290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
                325                 330                 335

Leu Asn Ser Thr Asn His Ala Ile Val Gln Thr Leu Val Asn Ser Val
            340                 345                 350

Asn Ser Lys Ile Pro Lys Ala Cys Cys Val Pro Thr Glu Leu Ser Ala
        355                 360                 365

Ile Ser Met Leu Tyr Leu Asp Glu Asn Glu Lys Val Val Leu Lys Asn
370                 375                 380

Tyr Gln Asp Met Val Val Glu Gly Cys Gly Cys Arg
385                 390                 395

<210> SEQ ID NO 2
<211> LENGTH: 431
<212> TYPE: PRT
<213> ORGANISM: Homo Sapiens

<400> SEQUENCE: 2

Met His Val Arg Ser Leu Arg Ala Ala Ala Pro His Ser Phe Val Ala
1               5                   10                  15

Leu Trp Ala Pro Leu Phe Leu Leu Arg Ser Ala Leu Ala Asp Phe Ser
                20                  25                  30

Leu Asp Asn Glu Val His Ser Ser Phe Ile His Arg Arg Leu Arg Ser
            35                  40                  45

Gln Glu Arg Arg Glu Met Gln Arg Glu Ile Leu Ser Ile Leu Gly Leu
        50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
```

```
            100                 105                 110
Thr Gln Gly Pro Pro Leu Ala Ser Leu Gln Asp Ser His Phe Leu Thr
            115                 120                 125

Asp Ala Asp Met Val Met Ser Phe Val Asn Leu Val Glu His Asp Lys
130                 135                 140

Glu Phe Phe His Pro Arg Tyr His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Gly Trp Leu
210                 215                 220

Val Phe Asp Ile Thr Ala Thr Ser Asn His Trp Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
        275                 280                 285

Arg Ser Ile Arg Ser Thr Gly Ser Lys Gln Arg Ser Gln Asn Arg Ser
290                 295                 300

Lys Thr Pro Lys Asn Gln Glu Ala Leu Arg Met Ala Asn Val Ala Glu
305                 310                 315                 320

Asn Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
        355                 360                 365

Ser Tyr Met Asn Ala Thr Asn His Ala Ile Val Gln Thr Leu Val His
370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
            420                 425                 430

<210> SEQ ID NO 3
<211> LENGTH: 501
<212> TYPE: PRT
<213> ORGANISM: Homo Sapiens

<400> SEQUENCE: 3

Met Arg Leu Pro Lys Leu Leu Thr Phe Leu Leu Trp Tyr Leu Ala Trp
1               5                   10                  15

Leu Asp Leu Glu Phe Ile Cys Thr Val Leu Gly Ala Pro Asp Leu Gly
                20                  25                  30

Gln Arg Pro Gln Gly Ser Arg Pro Gly Leu Ala Lys Ala Glu Ala Lys
            35                  40                  45

Glu Arg Pro Pro Leu Ala Arg Asn Val Phe Arg Pro Gly Gly His Ser
```

```
            50                  55                  60
Tyr Gly Gly Ala Thr Asn Ala Asn Ala Arg Ala Lys Gly Gly Thr
 65                  70                  75                  80

Gly Gln Thr Gly Gly Leu Thr Gln Pro Lys Asp Glu Pro Lys Lys
                 85                  90                  95

Leu Pro Pro Arg Pro Gly Gly Pro Glu Pro Lys Pro Gly His Pro Pro
                100                 105                 110

Gln Thr Arg Gln Ala Thr Ala Arg Thr Val Thr Pro Lys Gly Gln Leu
                115                 120                 125

Pro Gly Gly Lys Ala Pro Lys Ala Gly Ser Val Pro Ser Ser Phe
130                 135                 140

Leu Leu Lys Lys Ala Arg Glu Pro Gly Pro Pro Arg Glu Pro Lys Glu
145                 150                 155                 160

Pro Phe Arg Pro Pro Ile Thr Pro His Glu Tyr Met Leu Ser Leu
                165                 170                 175

Tyr Arg Thr Leu Ser Asp Ala Asp Arg Lys Gly Gly Asn Ser Ser Val
                180                 185                 190

Lys Leu Glu Ala Gly Leu Ala Asn Thr Ile Thr Ser Phe Ile Asp Lys
                195                 200                 205

Gly Gln Asp Asp Arg Gly Pro Val Val Arg Lys Gln Arg Tyr Val Phe
210                 215                 220

Asp Ile Ser Ala Leu Glu Lys Asp Gly Leu Leu Gly Ala Glu Leu Arg
225                 230                 235                 240

Ile Leu Arg Lys Lys Pro Ser Asp Thr Ala Lys Pro Ala Val Pro Arg
                245                 250                 255

Ser Arg Arg Ala Ala Gln Leu Lys Leu Ser Ser Cys Pro Ser Gly Arg
                260                 265                 270

Gln Pro Ala Ala Leu Leu Asp Val Arg Ser Val Pro Gly Leu Asp Gly
                275                 280                 285

Ser Gly Trp Glu Val Phe Asp Ile Trp Lys Leu Phe Arg Asn Phe Lys
290                 295                 300

Asn Ser Ala Gln Leu Cys Leu Glu Leu Glu Ala Trp Glu Arg Gly Arg
305                 310                 315                 320

Thr Val Asp Leu Arg Gly Leu Gly Phe Asp Arg Ala Ala Arg Gln Val
                325                 330                 335

His Glu Lys Ala Leu Phe Leu Val Phe Gly Arg Thr Lys Lys Arg Asp
                340                 345                 350

Leu Phe Phe Asn Glu Ile Lys Ala Arg Ser Gly Gln Asp Asp Lys Thr
                355                 360                 365

Val Tyr Glu Tyr Leu Phe Ser Gln Arg Arg Lys Arg Arg Ala Pro Leu
                370                 375                 380

Ala Thr Arg Gln Gly Lys Arg Pro Ser Lys Asn Leu Lys Ala Arg Cys
385                 390                 395                 400

Ser Arg Lys Ala Leu His Val Asn Phe Lys Asp Met Gly Trp Asp Asp
                405                 410                 415

Trp Ile Ile Ala Pro Leu Glu Tyr Glu Ala Phe His Cys Glu Gly Leu
                420                 425                 430

Cys Glu Phe Pro Leu Arg Ser His Leu Glu Pro Thr Asn His Ala Val
                435                 440                 445
```

-continued

```
Ile Gln Thr Leu Met Asn Ser Met Asp Pro Glu Ser Thr Pro Pro Thr
    450                 455                 460

Cys Cys Val Pro Thr Arg Leu Ser Pro Ile Ser Ile Leu Phe Ile Asp
465                 470                 475                 480

Ser Ala Asn Asn Val Val Tyr Lys Gln Tyr Glu Asp Met Val Val Glu
            485                 490                 495

Ser Cys Gly Cys Arg
            500
```

DEVICE HAVING OSTEOINDUCTIVE AND OSTEOCONDUCTIVE PROPERTIES

This application is the National Phase of International Application PCT/EP02/03463 filed 27 Mar. 2002 which designated the U.S. and that International Application was published under PCT Article 21(2) in English, and claims priority to European Application No. 01127573.2, filed Nov. 19, 2001.

The present invention relates to a device having osteoinductive and osteoconductive properties in vivo comprising a carrier containing calcium phosphate and an osteoinductive protein, wherein said carrier is homogeneously coated with said protein. Moreover, the present invention relates to a method for the production of a device having osteoinductive and osteoconductive properties in vivo. The invention encompasses a pharmaceutical composition comprising the device of the invention or a device which is obtainable by the method of the invention and relates to the use of said device for the preparation of a pharmaceutical composition to be used for bone augmentation, for treating bone defects, for treating degenerative and traumatic disc disease, for sinus floor elevation and for treatment of bone dehiscence. Finally, the invention relates to a kit comprising the device of the invention or a device which is obtainable by the method of the invention.

Various calcium phosphates such as beta-tricalcium phosphate ($Ca_3(PO_4)_2$) (beta-TCP), alpha-tricalcium phosphate (alpha-TCP) and hydroxy apatite (HA) have been shown to be effective as bone replacement materials. Beta-TCP, for example, is suitable both as granulate and in pieces (blocks) for the treatment of bone defects. The bone replacements materials containing calcium phosphate are usually used when the regeneration of the bone is not possible any more or is possible with difficulties only. In addition, bone replacement materials are used when the formation of additional bone is a prerequisite for a subsequent setting of an implant. The calcium phosphates exhibit an osteoconductive effect, i.e. they represent an inert structure facilitating the migration of cells from the neighbouring bone. The presence of bones or different mesenchymal cells, however, is a precondition for the new formation of bones. The effect of calcium phosphates can be significantly increased by adding bone chips. The bones are not only osteoconductive but also osteogenic (stimulation of bone cells for the neosynthesis of bone material) and osteoinductive, i.e. they cause the transformation of undifferentiated mesenchymal stem cells in osteoblasts and chondrocytes. For reasons of safety, autogenic bone chips are preferred to the allogenic or xenogenic preparations. The production of autogenic bones, however, always involves a second surgical procedure, which, in many cases, is not accepted by the patient.

An alternative to the use of autogenic bones is the use of specific bone growth and differentiation factors such as GDF-5 or different bone morphogenetic proteins (BMPs). These protein factors have an osteoinductive effect which, however, they can only exert if they are used in an immobilized form. In the literature, both calcium phosphates, collagen and mineralised collagen (collagen-containing calcium phosphate) are described as carriers (hydroxy apatite and beta-TCP (Hotz, 1994), hydroxylic apatite from algae extracts (Gao, 1996), bone extracts (Gombotz, 1996) and collagen (Friess, 1999). The analyses of the potency of the coated carriers, which are described in the literature, do not present a uniform picture but exhibit significant variations which are a consequence of either the carrier type selected or the coating method (Terheyden et al. (1997)). Various methods are described. In WO 98/21972 coating is achieved by rapid precipitation of GDF-5 onto beta-TCP is achieved by first dissolving GDF-5 in an organic solvent and then precipitating it by adding water. Due to the toxicity of many solvents, however, such a process is not preferred for the production of pharmaceutical compositions. Lind et al. (1996) carry out the coating of various calcium phosphate ceramics in the presence of gelatine (usually obtained from bovine or pig bones) as protection protein. Due to the increased risk of infection, however, the use of animal substances should be avoided for the production of pharmaceutical compositions and medicinal products. Friess et al. (1999) and Gao et al. (1996) describe the coating of collagens with BMP-2. Due to the low compressive strength of collagens, such carriers, however, are not suitable for all indications. This particularly applies to indications with which the newly-formed bone has to sustain a later pressure load. Furthermore, pharmaceutical qualities of collagen are so far available from animal sources only.

Although several papers describe the use of protein coated carriers for bone augmentation, efficient and reliable methods for manufacturing and use for treating bone defects are not available but nevertheless highly desirable.

Thus, the technical problem underlying the present invention is to provide means and methods for efficiently and reliably treating bone defects comprising bone augmentation.

The technical problem is solved by the embodiments characterized in the claims.

Accordingly, the present invention relates to a device having osteoinductive and osteoconductive properties in vivo comprising a carrier containing calcium phosphate and an osteoinductive protein, wherein said carrier is homogeneously coated with said protein.

The term "device" as used in accordance to the present invention refers to a entity which comprises at least two components. One of said components is a carrier matrix. Preferably, said carrier matrix consists of inorganic ceramics. Said ceramics have a particularly high surface due to the presence of macro- and micro pores. Preferably, said macro- pores have a diameter of approximately 100 to 400 nm while the micro- pores have a diameter of less than 10 nm. Most preferably, said carrier is a calcium phosphate as referred to infra.

Another component of said device is a protein or polypeptide which has osteoinductive properties as will be explained in detail below. The protein or polypeptide is immobilized on the surface of the carrier. The osteoinductive proteins and polypeptides applied in accordance with the present invention have a particular high affinity for inorganic carrier matrices such as calcium phosphate. Preferably, the binding of said protein or polypeptide to the carrier is reversible. Thereby, dissolution of said protein is allowed once the device has been brought into a suitable in vivo surrounding, such as a bone cavity. Preferably, said dissolution of the proteins is slow release allowing diffusion of the protein into the tissue which surrounds the device. Thus, the device serves as an in vivo source for osteoinductive proteins which are slowly released and which can be thereby efficiently distributed into the surrounding tissues or have an effect in the immobilized form.

The device may, moreover, comprise additional excipients. These excipients serve to stabilization of the protein, e.g., saccharides, amino acids, polyols or detergents or maintenance of the pH, e.g., buffer substances. Preferred excipients encompassed by this invention are discussed in detail below.

The term "osteoinductive" refers to the capability of the transformation of mesenchymal stem cells into osteoblasts and chondrocytes. A prerequisite for osteoinduction is a signal which is distributed by the device into the surrounding tissues where the aforementioned osteoblast precursors become activated. Osteoinduction as used herein encompasses the differentiation of mesenchymal cells into the bone precursor cells, the osteblasts. Moreover, osteoinduction also comprises the differentiation of said osteoblasts into osteocytes, the mature cells of the bone. Moreover, also encompassed by osteinduction is the differentiation of mesenchymal cells into chondrocytes. In particular in the long bones, the chondroblasts and the chondrocytes residing in the perichondrium of the bone can also differentiate into osteocytes. Thus, osteoinduction requires differentiation of undifferentiated or less-differentiated cells into osteocytes which are capable of forming the bone. Thus, a prerequisite for osteoinduction is a signal which is distributed by the device into the surrounding tissues where the aforementioned osteocyte precursors usually reside. As has been described above, the osteoinductive proteins used in accordance with the present invention are slowly released from the device after implantation and are distributed efficiently in the surrounding tissues. Moreover, the proteins and polypeptides encompassed by the present invention have osteoinductive properties in vivo. For example, it is well known in the art that the Transforming Growth Factor-β (TGF-β) superfamily encompasses members which have osteoinductive properties. Individual members of said TGF-β superfamily which have particular well osteoinductive properties are listed infra. In conclusion, the osteoinductive proteins of the device of the present invention after having been released from the carrier serving as a osteoinductive signal for the osteocyte precursors of the tissue surrounding the side of implantation of the device.

The term "osteogenic" describes the synthesis of new bone by osteoblasts. In accordance with the present invention, pre-existing bone in the surrounding of the side of implantation of the device grows into the device using the structure of the device as a matrix onto which the osteocytes can adhere.

The term "carrier" encompasses three dimensional matrices, such as the ceramics referred to above. Moreover, as described above, said carrier, preferably, has an enlarged surface due to formation of macro- and micro-pores. The carrier material has a high affinity for osteoinductive proteins but nevertheless allows release of said proteins in vivo. In accordance with the present invention, said carrier is, preferably, a calcium phosphate. The carrier comprised by the device of the invention may be brought into a suitable from for administration of the device in vivo, such as ceramics in form of granules, blocks, cubes, cements and amorphic pastes. In addition, the carrier may be coated onto a metallic surface.

The term "calcium phosphate" encompasses compositions comprising calcium ions, phosphate ions and, optionally, further ions or atoms which are suitable for the carrier of the present invention. The calcium phosphates as used in accordance with the present invention are crystals having a three dimensional structure suitable for the device of the present invention as set forth above. A list of preferred and well known calcium phosphates is given infra.

The term "osteoinductive protein" as set forth above, refers to Transforming Growth Factor-β (TGF-β) superfamily members which have osteoinductive properties, such as Growth and Differentiation Factor-5; see infra. These osteoinductive proteins exhibit a high affinity to calcium phosphates. Calcium phosphate can be present e.g. in the form of beta-TCP, α-TCP or hydroxy apatite. Depending on the macro-(100-400 nm) and micropores (<10 nm), these inorganic minerals absorb aqueous solutions. During this process, proteins such as GDF-5 or BMP-2 are adsorbed tightly onto the surface of the carrier. An important precondition for this process is a sufficient solubility of the proteins in the coating solution The term "homogeneously coated" means that the surface of the carrier is entirely coated with the said osteoinductive protein, whereby essential identical amounts of protein are present in each and every area of the surface of said carrier. A homogeneously coated carrier in accordance with this invention, preferably, exhibits a maximum covering with the osteoinductive protein on its surface. Homogenous coating is a prerequisite for efficient release and homogenous distribution and activity of the osteoinductive protein into the tissue surrounding the site of implantation. Moreover, it is to be understood that the osteoinductive proteins are not aggregated and partially or entirely inactivated due to precipitation or micro-precipitation, rather attachment of biologically active, non-aggregated proteins is to be achieved by homogenous coating. Said homogenous coating can be achieved by the method of the present invention and as described in the accompanied Examples. Further, means and methods for controlling homogeneous coating, quantification and characterization of the immobilized protein are described in the accompanied Examples.

Advantageously, it has been found in accordance with the present invention that the above described device of the present invention has improved and reliable osteoinductive and osteoconductive properties in vivo after implantation into a subject, preferably a human. A prerequisite for such a device is a homogenous coating of the carrier with biologically active, non-aggregated osteoinductive protein. It has been found that even aggregation caused by micro-precipitation leads to an inhomogenous coat resulting in at least significantly decreased osteoinductive properties as described for other devices in the prior art, e.g., in WO98/21972.

Moreover, it has been found that undesirable side effects, such as inflammation and toxic reactions of the subject after implantation, can be avoided by the device of the present invention which is free of toxic impurities or infectious contaminants. In particular, the use of protecting proteins (such as e.g. gelatine) as solubility mediator is totally unnecessary for the device of the present invention.

Moreover, the present invention relates to a method for the production of a device having osteoinductive and osteoconductive properties in vivo comprising the steps of:
(a) providing a solution comprising dissolved osteoinductive protein and a buffer which keeps said protein dissolved for a time sufficient to allow homogenous coating of a carrier containing calcium phosphate when brought into contact with said carrier;
(b) contacting the solution of step (a) with a carrier containing calcium phosphate;
(c) allowing homogenous coating of the surface of said carrier with said dissolved protein; and
(d) drying of the coated carrier obtained in step (c).

The definitions of the terms used to describe the device of the invention apply mutatis mutandis to the aforementioned method and the methods referred to below.

The term "drying" encompasses means for removing liquids, such as excess buffer solution, which are still present after coating of the carrier with the osteoinductive protein. Preferably, drying is achieved by vaccum- or freeze-drying.

The term "buffer which keeps said protein dissolved for a time to allow homogenous coating" refers to a buffer in which the osteoinductive proteins can be efficiently dissolved and which is capable of balancing the increase of pH caused by contacting the buffer solution with the calcium phosphate carrier so that the protein does not immediately precipitate, e.g., due to a pH increase. Said buffer can be composed by the person skilled in the art based on the solubility of the osteoinductive protein which depends on the pH, the ionic strength and the influence of the carrier on said parameters after contacting the carrier with said buffer solution. In accordance with the present invention it has been found that a suitable buffer for the method of the present invention comprises a buffer substance in a low concentration, a weak acid, an alcohol or a saccharide.

An advantage of the present invention is the homogenous coating which is achieved by limitation of the pH increase of the coating solution during the coating process. The described process allows the homogenous distribution and immobilization of the osteoinductive protein onto the said carrier. The efficacy of the coating process is, furthermore, supported by the carrier due to capillary forces resulting from the presence of the numerous macro- and micro-pores which due to their size are capable of soaking the solution into the pores. Moreover, in contrast to other methods described in the art, e.g., in WO98/21972, the osteoinducitve protein or polypeptide is according to the method of the present invention applied by attachment to the carries rather than by precipitation or micro-precipitation. The findings underlying the present invention demonstrate that the aggregation of the proteins can be avoided by the use of suitable additives as described herein. An important precondition is the knowledge of the solubility of the osteoinductive protein dependent on the pH value, ionic strength and surfaces present. The slowing down of the pH increase caused by the contact of coating solution with the calcium phosphates reacting in an alkaline manner, in particular, plays an important role during the coating. Advantageously, by the method of the present invention, distributing evenly across the inner surface of the carrier material and being able to bind to the surfaces before a pH-induced precipitation of the said protein takes place. It could be demonstrated that the pH increase taking place during the coating of calcium phosphates is decelerated sufficiently by the use of a weak acid, such as acetic acid. Furthermore, the addition of organic combinations such as ethanol or sucrose proves to be additionally advantageous. Furthermore, a low ionic strength are an important precondition for successful coating. Moreover, our tests show that the volume of the coating solution, too, has a considerable effect on the quality of the coating. Finally, the method of the present invention aims to avoid harmful organic solvents, such as acetonitrile, which are routinely used in the methods described in the art. By avoiding said harmful organic solvents, the safety profile and local tolerability of the device of the present invention can be improved.

In a preferred embodiment of the method of the invention said buffer has a buffer concentration of less than 100 mmol/l, less than 50 mmol/l or less than 20 mmol/l.

It follows from the above that more preferably, said buffer contains a weak acid. The term "weak acid" refers to organic or inorganic compounds containing at least one ionogenically bound hydrogen atom. Weak acids are well known in the art and are described in standard text books, such as Römpp, lexicon of chemistry. Preferably, said weak acids which have low dissociation degrees and are described by pK values between 3 and 7, preferred between 4 and 6.

Most preferably, said weak acid is acetic acid or succinic acid.

In another preferred embodiment of the method of the invention said buffer further comprises saccharides.

The term "saccharides" encompasses mono-, di- and polysaccharides. The structure and composition of mono-, di, and polysaccharides are well known in the art and are described in standard text books, such as Römpp, lexicon of chemistry.

More preferably, said saccharide is a disaccharide. Most preferably, said dissaccharide is sucrose or trehalose.

In a further preferred embodiment of the method of the invention said buffer comprises an alcohol.

Suitable alcohols are well known in the art and are described in standard text books, such as Römpp, lexicon of chemistry.

More preferably, said alcohol is ethanol or mannitol.

In a preferred embodiment of the device or the method of the invention said calcium phosphate is beta tricalcium phosphate, alpha tricalcium phosphate, apatite or a calcium phosphate containing cement.

Said calcium phosphates are particularly well suited as carriers for the device of the present invention. Their in vivo properties have been described in Hotz, 1994, Gao, 1996, and in WO98/21972.

In a further preferred embodiment of the device or the method of the invention said osteoinductive protein is a member of the TGF-β family.

The TGF-β family of growth and differentiation factors has been shown to be involved in numerous biological processes comprising bone formation. All members of said family are secreted polypeptides comprising a characteristic domain structure. On the very N-terminus, the TGF-β family members comprise a signal peptide or secretion leader. This sequence is followed at the C-terminus by the prodomain and by the sequence of the mature polypeptide. The sequence of the mature polypeptide comprises seven conserved cysteines, six of which are required for the formation of intramolecular disulfide bonds whereas one is required for dimerization of two polypeptides. The biologically active TGF-β family member is a dimer, preferably composed of two mature polypeptides. The TGF-β family members are usually secreted as proproteins comprising in addition to the mature sequence the prodomain. The prodomains are extracellularly cleaved off and are not part of the signalling molecule. It has been reported, however, that the prodomain(s) may be required for extracellular stabilization of the mature polypeptides.

In the context of the present invention, the term "TGF-β family member" or the proteins of said family referred to below encompass all biologically active variants of the said proteins or members and all variants as well as their inactive precursors. Thus, proteins comprising merely the mature sequence as well as proteins comprising the mature protein and the prodomain or the mature protein, the prodomain and the leader sequence are within the scope of the invention as well as biologically active fragments thereof. Whether a fragment of a TGF-β member has the biological activity can be easily determined by biological assays described, e.g. in: Katagiri T, Yamaguchi A, Ikeda T, Yoshiki S, Wozney J M, Rosen V, Wang E A, Tanka H, Omura S, Suda T, (1990): The non-osteogenic mouse pluripotent cell line, C3H10T1/2, is induced to differentiate into osteoblastic cells by recombinant human bone morphogenetic protein-2. Biochem. Biophys. Res. Commun. 172: 295-299 or Nishitoh H, Ichijo H, Kimura M, Matsumoto T, Makishima F, Yamaguchi A, Yamashita H, Enomoto S, Miyazono K (1996): Identification of type I and type II serine/threonine kinase receptors for growth/differentiation factor-5. J. Biol. Chem. 271: 21345-21352.

Preferably, the biological activity according to the invention can be determined by in vivo models as described in the accompanied Examples. Furthermore, encompassed by the present invention are variants of the TGF-β members which have an amino acid sequences being at least 75%, at least 80%, at least 90%, at least 95%, at least 96%, at least 97%, at least 98% or at least 99% identical to the amino acid sequences of the members of the TGF-β family.

An overview of the members of the TGF-β superfamily is given in: Wozney J M, Rosen V (1998): Bone morphogenetic protein and bone morphogenetic protein gene family in bone formation and repair. Clin Orthop 346: 26-37. The amino acid sequences of the members of the TGF-β family can be obtained from the well known databases such as Swiss-Prot via the internet (http://www.expasy.ch/sprot/sprot-top.html) Amino acid sequences for BMP2, BMP7 and GDF-5, members of the TGF-β family with a particularly high osteoinductive potential, are also shown in SEQ ID No: 1 to 3, respectively. Amino acid sequences for BMP2, BMP7 and GDF-5, members of the TGF-β family with a particularly high osteogenic potential, are also shown in SEQ ID No:1 to 3, respectively.

More preferably, said member of the TGF-β family is a member of the BMP subfamily.

The members of the Bone Morphogenetic Protein (BMP) subfamily have been shown to be involved, inter alia, in the induction and re-modelling of bone tissue. BMPs were originally isolated from bone matrix. These proteins are characterized by their ability to induce new bone formation at ectopic sites. Various in vivo studies demonstrated the promotion of osteogenesis and chondrogenesis of precursor cells by BMPs and raise the possibility that each BMP molecule has distinct role during the skeletal development. More details about the molecular and biological properties of the BMPs are described in:

Wozney J M, Rosen V (1998): Bone morphogenetic protein and bone morphogenetic protein gene family in bone formation and repair. Clin Orthop 346: 26-27, Schmitt J, Hwang K, Winn, S R, Hollinger J (1999): Bone morphogenetic proteins: an update on basic biology and clinical relevance. J Orthop Res 17: 269-278 and Lind M (1996): Growth factors: possible new clinical tools. A review. Acta Orthop Scand 67: 407-17.

Most preferably, said member of the BMP family is BMP2 or BMP7.

The amino acid sequence for the preproform of BMP2 is deposited under Swiss-Prot Accession number P12643 and is shown below. Amino acids 1 to 23 correspond to the signal sequence, amino acids 24 to 282 correspond to the propeptide and amino acids 283 to 396 correspond to the mature protein. The amino acid sequence for the preproform of BMP7 is deposited under Swiss-Prot Accession number P18075 or shown in SEQ ID No: 2. Amino acids 1 to 29 correspond to the leader sequence, amino acids 30 to 292 correspond to the proform and amino acids 293 to 431 correspond to the mature protein. Preferably, BMP-2 or BMP7 refers to the preproform, to the proform or to the mature BMP-2 or BMP-7 peptide, respectively. Moreover also encompassed are fragments of said proteins having essentially the same biological activity, prefrably osteoinductive properties. More sequence information for BMP2 and BMP7 is provided below.

Also more preferably, said member of the TGF-β family is a GDF.

Growth and Differentiation Factor (GDF) have been also shown to be involved, inter alia, in the induction and re-modelling of bone tissue. Growth Differentiation Factor 5 (GDF-5), also known as cartilage-derived morphogenetic protein 1 (CDMP-1) is a member of subgroup of the BMP family, which also includes other related proteins, preferably, GDF-6 and GDF-7. The mature form of the protein is a 27 kDa homodimer. Various in vivo and in vitro studies demonstrate the role of GDP-5 during the formation of different morphological features in the mammalian skeleton. Mutations of GDF-5 are responsible for skeletal abnormalities including decrease of the length of long bones of limbs, abnormal joint development in the limb and sternum (Storm & Kingsley (1999), Development Biology, 209, 11-27). The amino acid sequence between mouse and human is highly conserved.

Most preferably, said member of the GDF subfamily is GDF-5.

The amino acid sequence for the preproform of GDF-5 is deposited under Swiss-Prot Accession number P 43 0 26 or shown in SEQ ID No: 3. Amino acids 1 to 27 correspond to the leader sequence, amino acids 28 to 381 correspond to the proform and amino acids 382 to 501 correspond to the mature protein. Preferably, GDF-5 refers to the preproform, to the proform or to the mature GDF-5 peptide. Moreover also encompassed are fragments of GDF-5 having essentially the same biological activity, prefrably osteoinductive properties. Most preferably, said fragment comprises amino acids 383 to 501 of the sequence shown in SEQ ID No: 3.

In another preferred embodiment of the device or the method of the invention said device is free of toxic substances.

The term "toxic substances", preferably, encompasses those toxic organic solvents and additives which are used by the methods described in the art, e.g. actetonitrile. Said substances may cause inflammation and other reactions after implantation of devices containing said substances. Said devices are therapeutically less acceptable due to said undesirable side effects which can not be avoided by the coating methods described in the art. Moreover, the international guidance for the development of therapeutic proteins require that in the manufacturing process harmful and toxic substances should be avoided (for details see: International Conference on Harmonisation (ICH), Topic Q3C; www. emea.e-u.int/). However, the device of the present invention or a device which is obtainable by the method of the present invention is, advantageously, free of said toxic substances and, therefore, therapeutically well acceptable and fulfills the requirements of the regulatory authorities.

Moreover, in a further preferred embodiment of the device or the method of the invention said device is free of infectious material.

Besides toxic substances, infectious material comprised by the device may cause severe infections in a subject into which the device has been transplanted. Potentially infectious gelatin derived from bovine or procine bones is, however, used as a protecting protein in many state of the art methods (Lind, 1996).

The invention encompasses a pharmaceutical composition comprising the device of the invention or a device which is obtainable by the method of the invention.

The product of the present invention can be formulated as a pharmaceutical composition or a medical device. The composition of said product may comprise additional compounds like stabilizers, buffer substances and other excipients. The amount of the product of the present invention applied to the patient will be determined by the attending physician and other clinical factors; preferably in accordance with any of the above described methods. As it is well known in the medical arts, the amount applied to a patient depends upon many factors, including the patient's size, body surface area, age, sex, time and route of administration, general health, and other drugs being administered concurrently. Progress can be monitored by periodic assessment.

Thanks to the present invention, it is possible to treat various bone defects including large cavities. In particular, large cavities could not or only under use of autogenous bone material be efficiently treated. However, due to the reliable and efficient osteoinductive and the oseoconductive properties of the device of the present invention or a device which can be obtained by the method of the invention treatment of bone defects which requires extensive bone augmentation or repair has now become possible without a second surgery.

The invention also encompasses the use of the device of the invention or a device which is obtainable by the method of the invention for the preparation of a pharmaceutical composition to be used for bone augmentation.

The definitions of the terms referred to above apply mutatis mutandis to the aforementioned use of the present invention and those described infra.

The term "bone augmentation" refers to the therapeutic formation of bone, which is indicated in order to treat bone defects, cavities in bones, or diseases and disorders accompanied with loss of bone tissue or to prepare the subsequent setting of an implant. The diseases and disorders described in the following are well known in the art and are described in detail in standard medical text books such as Pschyrembel or Stedman.

Preferably, said bone augmentation follows traumatic, malignant or artificial defects.

Another embodiment of the present invention relates to the use of the device of the invention or a device which is obtainable by the method of the invention for the preparation of a pharmaceutical composition for treating bone defects.

More preferably, said bone defects are long bone defects or bone defects following apicoectomy, extirpation of cysts or tumors, tooth extraction, or surgical removal of retained teeth.

The invention also relates to the use of the device of the invention or a device which is obtainable by the method of the invention for filing of cavities and support guided tissue regeneration in periodontology.

Another embodiment of the present invention relates to the use of the device of the invention or a device which is obtainable by the method of the invention for the preparation of a pharmaceutical composition to be used for sinus floor elevation, augmentation of the atrophied maxillary and mandibulary ridge and stabilization of immediate implants.

Also within the scope of the present invention is a method for treating one or more of the diseases referred to in accordance with the uses of the present invention, wherein said method comprises at least the step of administering the device of the invention or a device which can be obtained by the method of the invention in a pharmaceutically acceptable form to a subject. Preferably, said subject is a human.

Finally, the invention relates to a kit comprising the device of the invention or a device which is obtainable by the method of the invention.

The parts of the kit of the invention can be packaged individually in vials or other appropriate means depending on the respective ingredient or in combination in suitable containers or multicontainer units. Manufacture of the kit follows preferably standard procedures which are known to the person skilled in the art.

The following tables show amino acid sequences for BMP-2, BMP-7 and GDF-5:

Human BMP-2 (Swiss-Prot Prim. Accession Number P12643); SEQ ID No. 1:

| Key | From | To | Length |
| --- | --- | --- | --- |
| SIGNAL | 1 | 23 | 23 |
| PROPEP | 24 | 282 | 259 |
| hBMP2 | 283 | 396 | 114 |

```
            10         20         30         40         50         60
             |          |          |          |          |          |
        MVAGTRCLLA LLLPQVLLGG AAGLVPELGR RKFAAASSGR PSSQPSDEVL SEFELRLLSM 70         80         90        100        110        120
             |          |          |          |          |          |
        FGLKQRPTPS RDAVVPPYML DLYRRHSGQP GSPAPDHRLE RAASRANTVR SFHHEESLEE 130        140        150        160        170        180
             |          |          |          |          |          |
        LPETSGKTTR RFFFNLSSIP TEEFITSAEL QVFREQMQDA LGNNSSFHHR INIYEIIKPA 190        200        210        220        230        240
             |          |          |          |          |          |
        TANSKFPVTR LLDTRLVNQN ASRWESFDVT PAVMRWTAQG HANHGFVVEV AHLEEKQGVS 250        260        270        280        290        300
             |          |          |          |          |          |
        KRHVRISRSL HQDEHSWSQI RPLLVTFGHD GKGHPLHKRE KRQAKHKQRK RLKSSCKRHP 310        320        330        340        350        360
             |          |          |          |          |          |
        LYVDFSDVGW NDWIVAPPGY HAFYCHGECP FPLADHLNST NHAIVQTLVN SVNSKIPKAC 370        380        390
             |          |          |
        CVPTELSAIS MLYLDENEKV VLKNYQDMVV    EGCGCR
```

References
[1] SEQUENCE FROM NUCLEIC ACID.
MEDLINE = 89072730; PubMed = 3201241;
Wozney J.M., Rosen V., Celeste A.J., Mitsock L.M., Whitters M.J., Kriz R.W., Hewick R.M., Wang E.A.;
"Novel regulators of bone formation: molecular clones and activities.";
Science 242:1528-1534 (1988).
[2] X-RAY CRYSTALLOGRAPHY (2.7 ANGSTROMS) OF 292-396.
MEDLINE = 99175323; PubMed = 10074410;
Scheufler C., Sebald W., Huelsmeyer M.;
"Crystal structure of human bone morphogenetic protein-2 at 2.7 A resolution.";
J. Mol. Biol. 287:103-115 (1999).

Human BMP-7 (Swiss-Prot Prim. Accession. Number: P18075);
SEQ ID No. 2:

| Key | From | To | Length |
|---|---|---|---|
| SIGNAL | 1 | 29 | 29 |
| PROPEP | 30 | 292 | 263 |
| hBMP-7 | 293 | 431 | 139 |

```
         10         20         30         40         50         60
          |          |          |          |          |          |
   MHVRSLRAAA PHSFVALWAP LFLLRSALAD FSLDNEVHSS FIHRRLRSQE RREMQREILS 70         80         90        100        110        120
          |          |          |          |          |          |
   ILGLPHRPRP HLQGKHNSAP MFMLDLYNAM AVEEGGGPGG QGFSYPYKAV FSTQGPPLAS 130        140        150        160        170        180
          |          |          |          |          |          |
   LQDSHFLTDA DMVMSFVNLV EHDKEFFHPR YHHREFRFDL SKIPEGEAVT AAEFRIYKDY 190        200        210        220        230        240
          |          |          |          |          |          |
   IRERFDNETF RISVYQVLQE HLGRESDLFL LDSRTLWASE EGWLVFDITA TSNHWVVNPR 250        260        270        280        290        300
          |          |          |          |          |          |
   HNLGLQLSVE TLDGQSINPK LAGLIGRHGP QNKQPFMVAF FKATEVHFRS IRSTGSKQRS 310        320        330        340        350        360
          |          |          |          |          |          |
   QNRSKTPKNQ EALRMANVAE NSSSDQRQAC KKHELYVSFR DLGWQDWIIA PEGYAAYYCE 370        380        390        400        410        420
          |          |          |          |          |          |
   GECAFPLNSY MNATNHAIVQ TLVHFINPET VPKPCCAPTQ LNAISVLYFD DSSNVILKKY

430
          |
   RNMVVRACGC            H
```

References
[1] SEQUENCE FROM NUCLEIC ACID, AND PARTIAL SEQUENCE.
TISSUE = Placenta;
MEDLINE = 90291971; PubMed = 2357959;
Oezkaynak E., Rueger D.C., Drier E.A., Corbett C., Ridge R.J., Sampath T.K., Oppermann H.;
"OP-1 cDNA encodes an osteogenic protein in the TGF-beta family.";
EMBO J. 9:2085-2093 (1990).
[2] SEQUENCE FROM NUCLEIC ACID.
MEDLINE = 91088608; PubMed = 2263636;
Celeste A.J., Iannazzi J.A., Taylor R.C., Hewick R.M., Rosen V., Wang E.A., Wozney J.M.;
"Identification of transforming growth factor beta family members present in bone-inductive protein purified from bovine bone.";
Proc. Natl. Acad. Sci. U.S.A. 87:9843-9847 (1990).
[3] X-RAY CRYSTALLOGRAPHY (2.8 ANGSTROMS) OF 293-431.
MEDLINE = 96149402; PubMed = 8570652;
Griffith D.L., Keck P.C., Sampath T.K., Rueger D.C., Carlson W.D.;
"Three-dimensional structure of recombinant human osteogenic protein 1: structural paradigm for the transforming growth factor beta superfamily.";
Proc. Natl. Acad. Sci. U.S.A. 93:878-883 (1996).

Human GDF-5 (Swiss-Prot Prim. Accession Number: P 43026);
SEQ ID NO. 3:

| Key | From | To | Length |
|---|---|---|---|
| SIGNAL | 1 | 27 | 27 |
| PROPEP | 28 | 381 | 354 |
| hGDF-5 | 382 | 501 | 120 |

```
         10         20         30         40         50         60
          |          |          |          |          |          |
   MRLPKLLTFL LWYLAWLDLE FICTVLGAPD LGQRPQGSRP GLAKAEAKER PPLARNVFRP
```

```
                    Human GDF-5 (Swiss-Prot Prim. Accession Number: P 43026);
                                         SEQ ID NO. 3:

70          80          90         100         110         120
          |           |           |           |           |           |
    GGHSYGGGAT  NANARAKGGT  GQTGGLTQPK  KDEPKKLPPR  PGGPEPKPGH  PPQTRQATAR 130         140         150         160         170         180
          |           |           |           |           |           |
    TVTPKGQLPG  GKAPPKAGSV  PSSFLLKKAR  EPGPPREPKE  PFRPPPITPH  EYMLSLYRTL 190         200         210         220         230         240
          |           |           |           |           |           |
    SDADRKGGNS  SVKLEAGLAN  TITSFIDKGQ  DDRGPVVRKQ  RYVFDISALE  KDGLLGAELR 250         260         270         280         290         300
          |           |           |           |           |           |
    ILRKKPSDTA  KPAVPRSRRA  AQLKLSSCPS  GRQPAALLDV  RSVPGLDGSG  WEVFDIWKLF 310         320         330         340         350         360
          |           |           |           |           |           |
    RNFKNSAQLC  LELEAWERGR  TVDLRGLGFD  RAARQVHEKA  LFLVFGRTKK  RDLFFNEIKA 370         380         390         400         410         420
          |           |           |           |           |           |
    RSGQDDKTVY  EYLFSQRRKR  RAPLATRQGK  RPSKNLKARC  SRKALHVNFK  DMGWDDWIIA 430         440         450         460         470         480
          |           |           |           |           |           |
    PLEYEAFHCE  GLCEFPLRSH  LEPTNHAVIQ  TLMNSMDPES  TPPTCCVPTR  LSPISILFID 490         500
          |           |
    SANNVVYKQY  EDMVVESCGC           R
```

References
[1] SEQUENCE FROM NUCLEIC ACID.
TISSUE = Placenta;
MEDLINE = 95071375; PubMed = 7980526;
Hoetten G., Neidhardt H., Jacobowsky B., Pohl J.;
"Cloning and expression of recombinant human growth/differentiation factor 5.";
Biochem. Biophys. Res. Commun. 204:646-652 (1994).
[2] SEQUENCE FROM NUCLEIC ACID.
TISSUE = Articular cartilage;
MEDLINE = 95050604; PubMed = 7961761;
Chang S., Hoang B., Thomas J.T., Vukicevic S., Luyten F.P., Ryba N.J.P., Kozak C.A., Reddi A.H., Moos M.;
"Cartilage-derived morphogenetic proteins. New members of the transforming growth factor-beta superfamily predominantly expressed in long bones during human embryonic development.";
J. Biol. Chem. 269:28227-28234 (1994).

The figures show:

FIG. 1: Solubility of GDF-5 in 5 mM acetic acid, 5 mM H3PO4/NaOH, 150 mM NaCl at different pH values.

Figure 2:
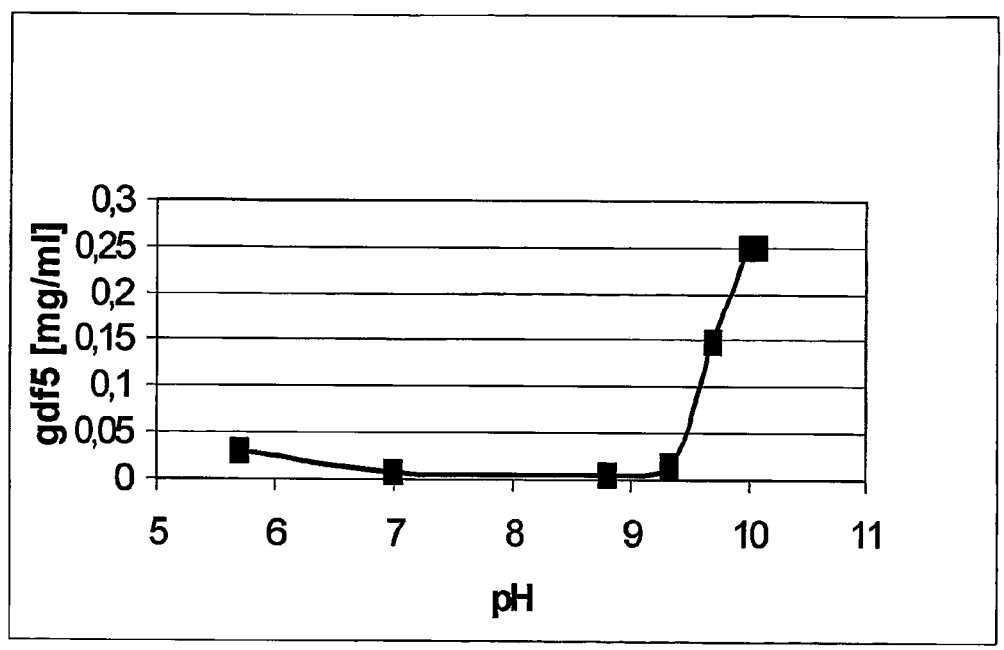

FIG. 2: Solubility of GDF-5 in 20 mM Arginin/acetic acid at different pH values.

Figure 3:
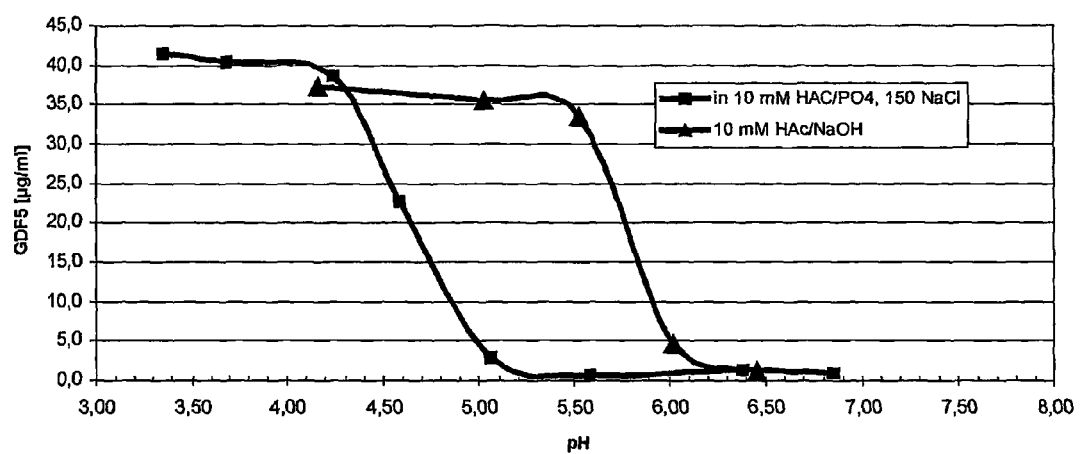

FIG. 3: Solubility of GDF-5 in two buffers having different ionic strength and pH values (HAc=acetic acid).

Figure 4:
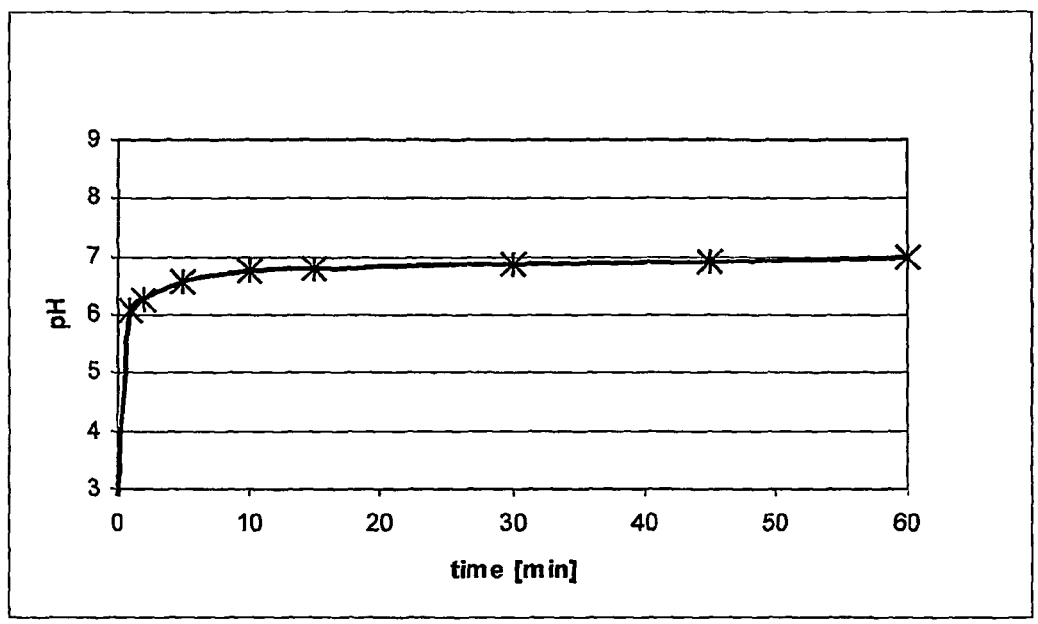

FIG. 4: Increase of the pH during coating in the presence of 10 mmol/l HCl.

Figure 5:
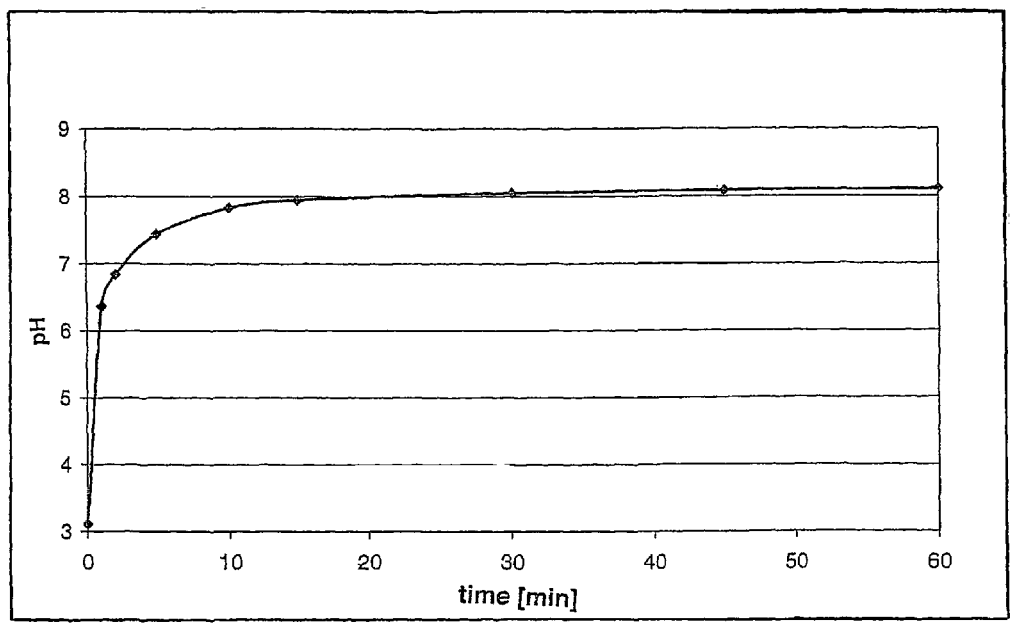

FIG. 5: Increase of the pH in the presence of 75% acetonitrile.

Figure 6:
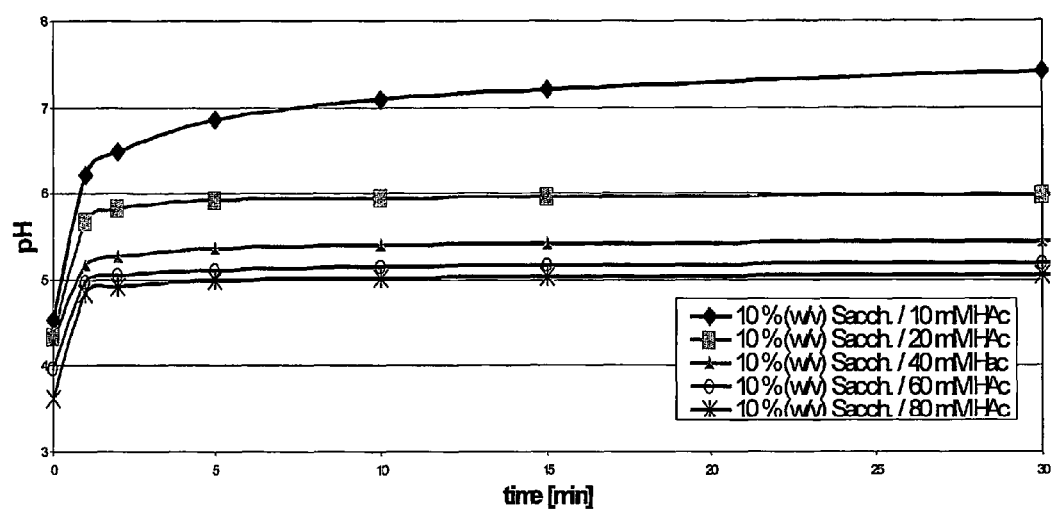

FIG. 6: Dependency of the pH of the coating solutions having different concentrations of acetic acid during coating.

Figure 7:

FIG. 7: Homogeneity of the distribution of GDF-5 on beta-TCP (100 μg GDF-5 on 100 mg beta-TCP) achieved by coating in the presence of 10 mmol/l acetic acid with (right) and without sucrose (left).

Figure 8:

FIG. 8: Homogeneity of the distribution of GDF-5 on beta-TCP (100 μg GDF-5 on 100 mg beta-TCP) achieved by coating in the presence of 60% ethanol.

Figure 9:

FIG. 9: Homogeneity of the distribution of GDF-5 on beta-TCP (100 μg GDF-5 on 100 mg beta-TCP) achieved by coating in the presence of 20 mmol/l glycin/NaOH, pH 10.

Figure 10:

FIG. 10: Histomorphometrical analysis of an implant coated in the presence of 20 mmol/l glycin/NaOH, pH10.

Figure 11:
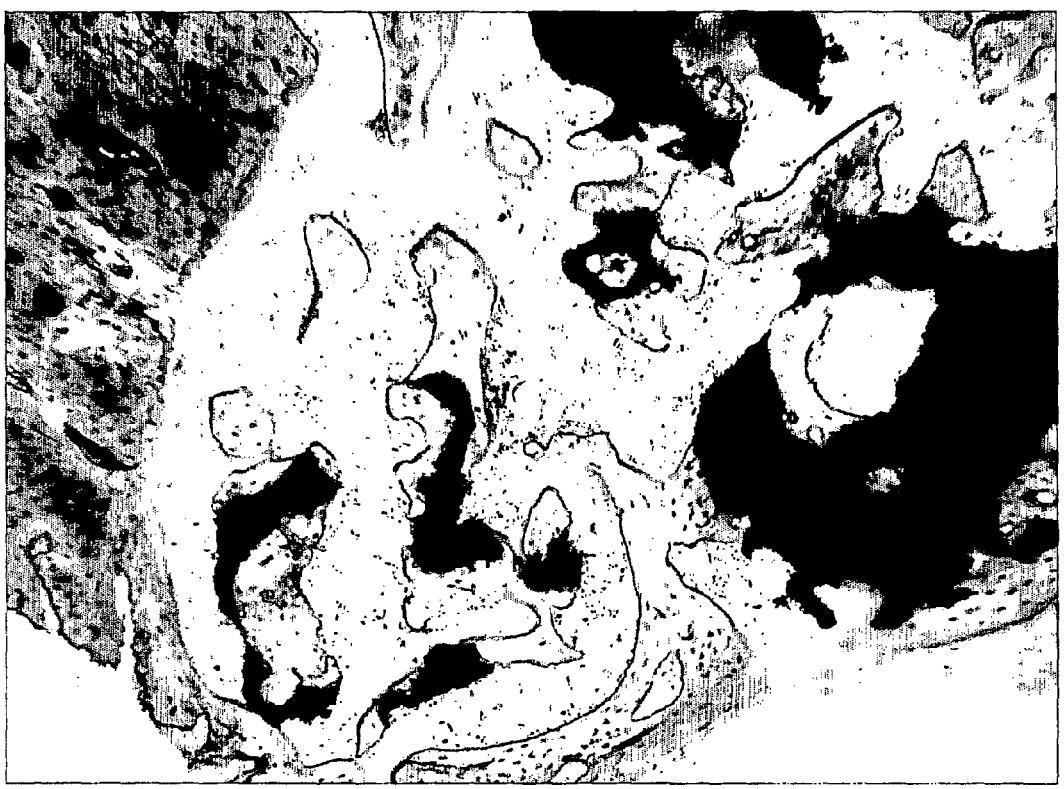

FIG. 11: Histomorphometrical analysis of an implant coated in the presence of 60% ethanol.

Figure 12:
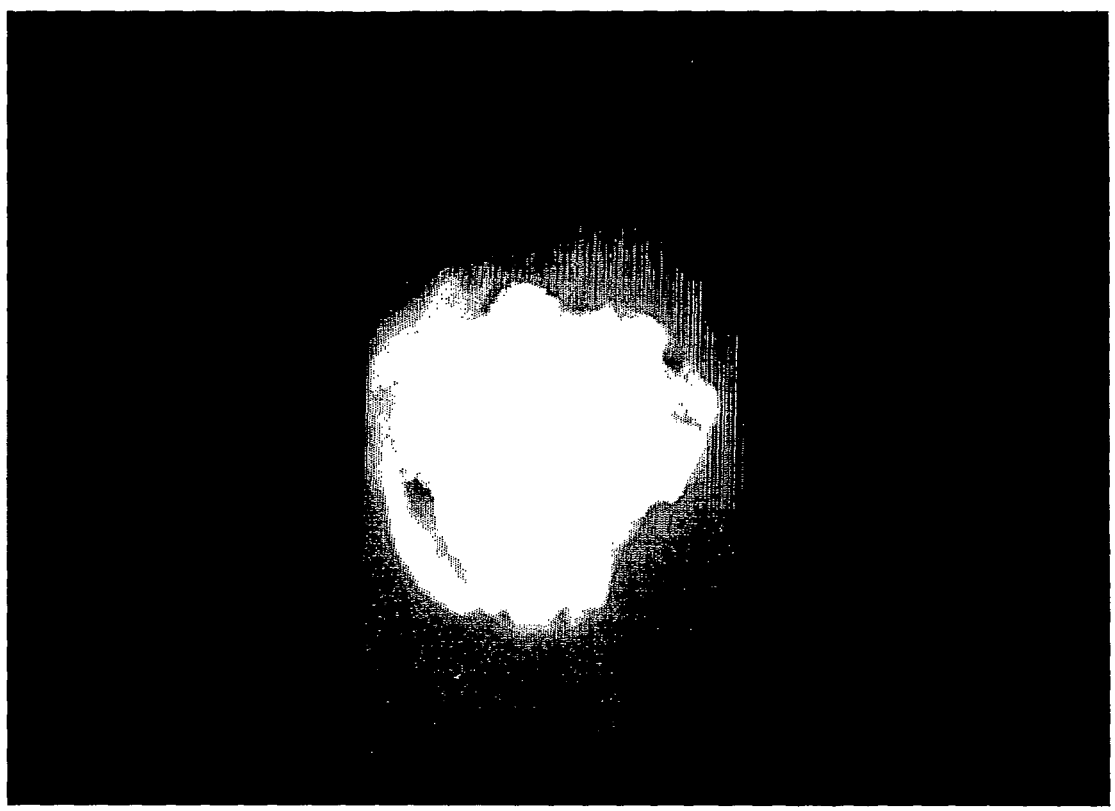

FIG. 12: Homogeneity of the distribution of rhBMP-2 on beta-TCP.

Figure 13:
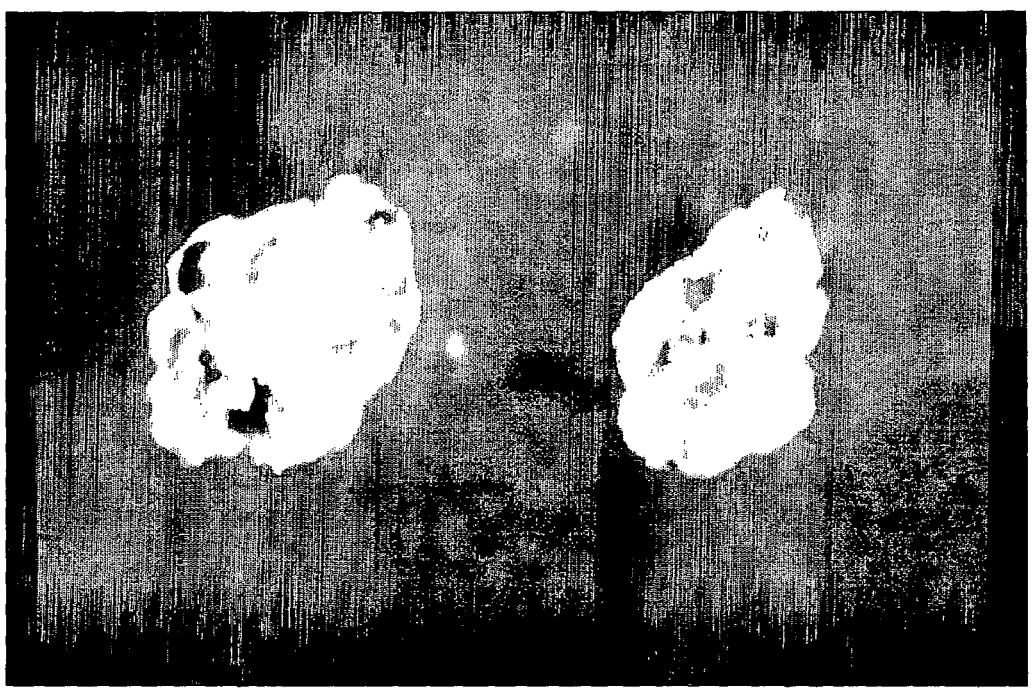

FIG. 13: Homogeneity of the distribution of GDF-5 on beta-TCP achieved by coating in the presence of sucrose (left) and trehalose (right).

Figure 14:
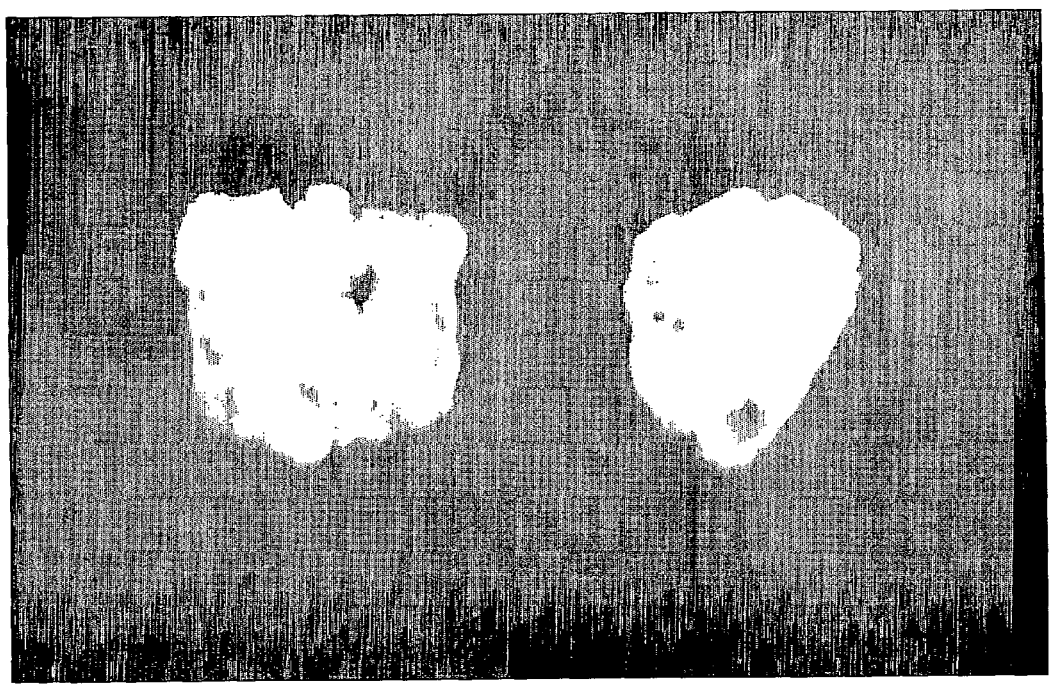

FIG. 14: Homogeneity of the distribution of GDF-5 on beta-TCP achieved by coating in the presence of ethanol (left) and mannitol (right).

The invention will now be described by reference to the following biological Examples which are merely illustrative and are not constructed as a limitation of the scope of the present invention.

EXAMPLE 1

Quantification of GDF-5 in Solution by RP-HPLC

The GDF-5 content was determined by reversed phase (RP-) HPLC-analysis. Aliquots of the sample were analysed using a Poros C8-18 column (R2/10, 2.1* 30 mm, Applied Biosystems). 0.1% formic acid in 21% acetonitrile (solvent A) and 0.1% formic acid in 84% acetonitrile (solvent B) were used as solvents at a flow rate of 0.4 ml/min. The elution profile was recorded by measuring the absorbance at 220 nm. The amounts of GDF-5 were calculated form the peak area at 220 nm using a standard curve.

EXAMPLE 2

Extraction and Quantification of the Immobilised Protein

Method A:

Coated beta-TCP (40 mg) were suspended in 700 µl solution matrix (1.22 mol/l citric acid, 1.22 mol/l HCl, 8 mol/l urea) and incubated for 60 min at 4° C. After centrifugation (13200* g, 2 min) 50 µl of the supernatant was analysed by RP_HPLC (see example 1). The standard curve was taken with various amounts of GDF-5 in the respective matrix solution.

Method B:

Coated beta-TCP (40 mg) were suspended in 700 µl solution matrix (10 mmol/l Tris/HCl, pH 7.4, 8 mol/l urea, 100 mmol/l EDTA) an incubated for 60 min at 4° C. and centrifuged (5 min at 13,500* g). Subsequently, the supernatant is quantified as described in method A or analysed further.

EXAMPLE 3

Solubility of rhGDF-5 at Different pH Values

GDF-5 is adjusted to a concentration of 4 mg/ml 10 mmol/l HCl. Aliquots (50 µl) of the stock solution are diluted 1:100 with 5 mmol/l acetic acid, 5 mmol/l $H_3PO_4$/NaOH, 150 mmol/l NaCl with different pH values each. The samples were incubated for 15 min and centrifuged (2 min at 13,200 * g). The pH value and the protein content in the supernatant were determined. In a second test, the stock solution was diluted with 20 mmol/l arginine/HOAc with different pH values each. The data in FIGS. 1 and 2 show that GDF-5 in buffers with low ionic strength (≤20 mmol/l) is soluble only in an acidic (pH≤5) or in an alkaline (>pH 10) solution. In the pH range of between 6.0 and 9.5, however, the solubility is <5 µg/ml.

EXAMPLE 4

Solubility of GDF-5 in Two Buffers Having Different Ionic Strength at Different pH Values GDF-5 is adjusted to a concentration of 4 mg/ml 10 mmol/l HCl. Aliquots (50 µl) of the stock solution are diluted 1:100 with 10 mmol/l acetic acid/NaOH and with 5 mmol/l acetic acid, 5 mmol/l $H_3PO_4$/NaOH, 150 mmol/l NaCl with different pH values each. The samples were incubated for 15 min and centrifuged (2 min at 13,200 * g). The pH value and the protein content in the supernatant are determined. The data in FIG. 3 show that with all the pH values measured, the solubility of GDF-5 in a buffer with higher ionic strength which corresponds to the physiological condition is significantly lower than in the buffer with low ionic strength (about 10 mmol/l).

EXAMPLE 5

Solubility of GDF-5 in Different Solvents

Freeze-dried GDF-5 was dissolved in pure acetonitrile, incubated for 15 min at room temperature and centrifuged (13,200* g, 2 min). No GDF-5 was detectable in the supernatant.

Freeze-dried GDF-5 (50 µg) was dissolved with 50 µl 75% acetonitrile, incubated for 15 min at room temperature and centrifuged (13,200 * g, 2 min). In the supernatant, the pH was measured and the content of GDF-5 was determined. 100% of the GDF-5 used were detected, the pH value of the solution was 3.0. Subsequently, the pH value was adjusted to pH 7.4 by adding NaOH, incubated for 15 min at room temperature again and centrifuged. Only 3 µg/ml corresponding to a solubility of 60 µg/ml, were detected.

The data show that GDF-5 is not soluble in pure acetonitrile but that it is soluble in acidic aqueous solutions containing acetonitrile. According to the results found in the aqueous systems, the solubility decreases in acetonitrile-water-mixtures with increasing pH.

EXAMPLE 6

Change of the pH Value of the GDF-5 Solution During the Coating of beta-TCP

In a reaction vessel, 200 mg beta-TCP are mixed with 200 µl of a coating solution containing GDF-5 (1 mg/ml; produced from a lyophilisate produced from a HCl solution). The pH value of the suspension is observed for 30 min. The results illustrated in FIGS. 4-5 show that after about 2 min, the pH of the suspension reaches the range of pH >6.5, which is critical for the solubility of GDF-5, when unbuffered coating solutions such as e.g. 10 mmol/l HCl or 75% acetonitrile are used (the acidic initial pH in 75% acetonitrile results from the remaining amounts of HCl present). Due to the insufficient solubility, precipitation of the protein and aggregation formation takes place which can be detected by means of Coomassie staining (see Example 7).

The use of an acetate-buffered coating solution (FIG. 6) causes a reduction of the pH increase during coating. While the pH increases to up to 8 in the unbuffered solutions, the pH of the acetate (40-80 mmol/l)-buffered coating solution reaches its maximum at pH 5.4. Thus, a sufficient solubility during the coating process is guaranteed. The GDF-5 used can spread evenly and bind to the carrier without precipitation taking place (see Example 7).

A delay of the pH increase is achieved also by using 60% ethanol. The delay is sufficient to achieve an even distribution of GDF-5 across the carrier (see Example 7).

EXAMPLE 7

Detection of the Homogeneity of the Coating

The adsorbed protein is made visible by staining with Coomassie Brilliant Blue on the carrier. The distribution of the blue colour correlates with the distribution of the respective protein on the beta-TCP carrier.

3-4 coated granules are incubated with 200 µl staining solution (60% PBS, 40% methanol, 0.4% Coomassie Brilliant Blue R250) in a cavity of a 96-well plate and incubated for 30 min at room temperature. An uncoated carrier is treated in the same way as control. The surplus staining agent is removed by washing with 60% PBS, 40% methanol until the uncoated carrier used as control is completely destained. The stained carrier is dried at 40° C. and documented photographically.

EXAMPLE 8

Coating of Granules (I)

200 mg β-TCP (0.5-1.0 mm granule size) are placed in a dry form in a 2R-glass. The stock solution of rhGDF-5 (4 mg/ml in 10 mM HCl) is diluted to 1 µg/ml with the means of the corresponding coating buffer. 200 µl of the GDF-5 solution obtained in that manner are pipetted on the beta-TCP and absorbed. The damp granulate is incubated for 1 hour at 25° C. and then vacuum-dried.

EXAMPLE 9

Coating of Granules (II)

200 mg β-TCP (0.5-1.0 mm granule size) are placed in a dry form in a 2R-glass. The stock solution of rhGDF-5 (4 mg/ml in 10 mM HCl) is diluted to 1 µg/ml with the means of the corresponding coating buffer. 200 µl of the GDF-5 solution obtained in that manner are pipetted on the beta-TCP and absorbed. The damp granulate is incubated for 1 hour at 25° C. and then lyophilised.

EXAMPLE 10

Coating of Blocks

A beta-TCP block having a mass of 360 mg is put into a suitable reaction vessel (Eppendorf), mixed with 500 µl of the coating solution, incubated for one hour and then vacuum- or freeze-dried.

EXAMPLE 11

Comparison of Different Coating Methods

Due to the use of acetate-buffered coating solutions, the precipitation formation could be reduced significantly. Another improvement was achieved by adding sucrose. The quality of the coating with and without sucrose is illustrated in FIG. 7. While individual precipitates can still be recognised as dark-blue spots without sucrose, the coating in the presence of sucrose results in a spot-free coating.

The significance of the homogeneity of the coating becomes clear comparing two preparations which were produced during the research using coating solutions in 60% ethanol and 20 mmol/l glycine/NaOH, pH 10, respectively. While a homogenous distribution was achieved in the presence of 60% ethanol (FIG. 8), a significant precipitation formation takes place on the carrier surface in the presence of glycine (FIG. 9). Both carriers were compared in a rat calvarial defect model (see below).

EXAMPLE 12

Full-thickness Calvarial Defect Model in Rats

Beta-TCP coated with rhGDF-5 (50 µg/25 mg of beta-TCP) was manufactured using different coating buffers (20 mmol/l glycin/NaOH, pH 10 (C1) and 60% ethanol (C2)). Rats were anaesthetized by intramuscular injection of Tiletamine-Zolazepam (ZOLETIL® VIRBAC, CARROS, France, 50 mg/kg, IM). The dorsal part of the cranium was clipped free of fur. Then, the skin was scrubbed with a germicidal soap (VETEDINE®, VETOQUINOL, LURE, France). The surgical site was scrabbed with an antiseptic such as Povidone iodine (VETEDINE® solution, VETOQUINOL, LURE, France). A 20 mm long incision in the scalp along the sagittal suture was realized and the skin, musculature and periosteum were reflected, exposing the parietal bones. A 6 mm trephined bur (COVELY, GENAY, France) was used to create the defect in the dorsal part of the parietal bone lateral to the sagittal suture under constant irrigation with sterile physiologic solution (AGUETTANT, LYON, France). Two identical defects were created per animal. Care was taken to prevent damage to the dura-mater and to prevent puncture of the superior sagittal sinus. After the implants were applied the periosteum and muscles were sutured in place and the scalp was sutured (polypropylene thread, Prolène®, ETHNOR, ISSY LES MOULINEAUX, France).

After a follow-up of 6 weeks, the animals were anesthetized by intramuscular injection of ZOLETIL® (50 mg/kg) then euthanatized by lethal dosis injection of DOLETHALND (Pentobarbital sodique, VETOQUINOL, LURE, France).

The explants were sampled and fixed in 10% buffered formalin solution. Afterwards samples were dehydrated in alcohol solutions of increased concentrations and embedded in PMMA (polymethylmetacrylate, Merck KGaA, Darmstadt, Germany). A section of 20 µm thickness was obtained by a microcutting and grinding technique adapted from Donath (Donath K. Breuner G., A method for the study of undecalcified bone and teeth with attached soft tissues. J. Oral. Pathol. 11, 318-326, 1982). A section was stained with modified Paragon for qualitative and semi-quantitative light microscopy analysis.

Histological sections were observed using a Polyvar microscope (REICHERT) fitted with a ×4, ×10, ×25 and ×40 objective.

Large amounts of bone marrow and osteoblastic cells were observed in the C2 treated site. In contrast, bone formation was poor with C1. Degradation of the implant material was also increased with C2 as compared to C1. For the results of the histomorphometrical analyses of the implant materials see Table 1 and FIGS. 10 and 11.

TABLE 1

| Sample | Bone tissue % | Implant % | Lacunae tissue % | Fibrous tissue % |
|---|---|---|---|---|
| C1 | 8.9 | 39.2 | 2.1 | 49.8 |
| C2 | 43.4 | 18.5 | 21.4 | 16.7 |

EXAMPLE 13

Coating of beta-TCP with BMP-2

200 mg beta TCP (0.5-1.0 mm granule size) are filled in a 2R-glass. The stock solution of BMP-2 is diluted to 1 mg/ml with the corresponding coating buffer (10 mmol/l acetic acid, 10% sucrose). 200 µl of the coating solution are incubated with the beta-TCP (1 hr, 4° C.) and freeze dried. The distribution of BMP-2 on the coated carrier was shown by Commassie staining (FIG. 12).

EXAMPLE 14

Comparison of the Coating Process in the Presence of Sucrose and Trehalose 200 mg beta-TCP (0.5-1.0 mm granule size) are filled in a 2R-glass. The stock solution of GDF-5 (4 mg/ml in 10 mmol/l HCl) is diluted to 1 mg/ml with the corresponding coating buffer. The two variants of the coating buffer are containing 10% sucrose and 10% trehalose, respectively. 200 µl of the coating solution are incubated with the beta-TCP (1 hr, 4° C.) and freeze dried. The distribution of GDF-5 on the coated carrier was shown by Commassie staining (FIG. 13).

EXAMPLE 15

Comparison of the Coating in the Presence of Ethanol and Mannitol 200 mg beta-TCP (0.5-1.0 mm granule size) are filled in a 2R-glass. The stock solution of GDF-5 (4 mg/ml in 10 mmol/l HCl) is diluted to 1 mg/ml with the corresponding coating buffer. The two variants of the coating buffer contain 60% ethanol and 10% mannitol, 10 mmol/l acetic acid, respectively. 200 µl of the coating solution are incubated with the beta-TCP (1 hr, 4° C.) and freeze dried. The distribution of GDF-5 on the coated carrier was shown by Commassie staining (FIG. 14).

REFERENCES

Celeste A. J., et al. (1990) "Identification of transforming growth factor . . . "; Proc. Natl. Acad. Sci. U.S.A. 87:9843-9847.
Chang, S. et al. (1994); "Cartilage-derived morphogenetic proteins . . . "; J. Biol. Chem. 269: 28227-28234.
EMEA, ICH Topic Q 3 C, Impurities: Residual Solvents
Friess, W. et al. (1998); Pharm. Dev. Technol. 4, 387-396.
Gao, T et al. (1996); Int. Orthopaedics 20, 321-325.
Gombotz, W et al. (1996) in Formulation, characterization and stability of protein drugs, Plenum Press, New York, USA, pp 219-245.
Griffith, D. L. et al. (1996); "Three-dimensional structure of recombinant human . . . "; Proc. Natl. Acad. Sci. U.S.A. 93: 878-883.
Hoetten, G. et al. (1994); "Coning and expression of recombinant human growth/differentiation factor 5."; Biochem. Biophys. Res. Commun. 204: 646-652.
Hotz, G et al. (1994); Int. J. Oral Maxillofac. Surg. 23, 413-417.
Katagiri, T. et al. (1990); Biochem. Biophys. Res. Commun. 172: 295-299.
Lind, M et al. (1996); J. Orthopaedic Res. 14, 343-350
Lind, M. (1996); Acta. Orthop. Scand. 67: 407-17.
Nishitoh, H. et al (1996); J Biol. Chem. 271: 21345-21352.
Oezkayanak, E. et al. (1990); "OP-1 cDNA encodes an osteogenic protein in the TGF-beta family"; EMBO J. 9: 2085-2093
Scheufler, C. et al. (1990); "Crystal structure of human bone morphogenetic protein-2 at 2.7 A resolution".
Schmitt, J. et al. (1999); J. Orthop. Res. 17: 269-278.
Shore, E. M. et al. (1997); "Human bone morphogenetic protein-2 (BMP-2) genomic DNA sequence".
Storm & Kingsley (1999); Development Biology, 209, 11-27.
Terheyden, H et al. (1997); Mund Kiefer Gesichtschir. 1, 272-275.
Wang, E. A. et al. (1990); "Identification of transforming growth factor beta family members present in bone-inductive protein purified from bovine bone."; Proc. Natl. Acad. Sci. U.S.A. 87: 9843-9847.
Wozney, J. M. et al. (1998); Clin. Orthop. 346: 26-37.
Wozney, J. M. et al. (1988); Science 242: 1528-1534.

---

The invention claimed is:

1. A device having osteoinductive and osteoconductive properties in vivo comprising a carrier containing calcium phosphate and a GDF-5 protein, wherein said carrier is entirely coated with said GDF-5 protein whereby identical amounts of said GDF-5 protein are present in each and every area of the surface of said carrier.

2. The device of claim 1, wherein said calcium phosphate is beta tricalcium phosphate, alpha tricalcium phosphate, hydroxyapatite, or a calcium phosphate containing cement.

3. The device of claim 1, wherein said device is free of toxic substances.

4. The device of claim 1, wherein said device is free of infectious material.

5. A pharmaceutical composition comprising the device of claim 1.

6. A kit comprising the device of claim 1.

7. A device having osteoinductive and osteoconductive properties in vivo comprising a carrier containing calcium phosphate and a GDF-5 protein, wherein said carrier is entirely coated with said GDF-5 protein whereby essentially identical amounts of said GDF-5 protein are present in each and every area of the surface of said carrier, obtainable by a method comprising the steps of:

(a) providing a solution comprising dissolved GDF-5 protein and a buffer containing a weak acid having a pK value between 3 and 7, wherein said buffer keeps said protein dissolved for a time sufficient to allow homogenous coating of a carrier containing calcium phosphate when brought into contact with said carrier and said buffer being capable of balancing the increase of pH caused by contacting the buffer solution with the calcium phosphate carrier so that the GDF-5 protein does not immediately precipitate because of said pH increase;

(b) contacting the solution of step (a) with a carrier containing calcium phosphate;

(c) allowing homogenous coating of the surface of said carrier with said dissolved protein; and (d) drying of the coated carrier obtained in step (c).

8. The device of claim 7, wherein the pK value is between 4 and 6.

9. The device of claim 7, wherein said calcium phosphate is beta tricalcium phosphate, alpha tricalcium phosphate, hydroxyapatite, or a calcium phosphate containing cement.

10. The device of claim 7, wherein said device is free of toxic substances.

11. The device of claim 7, wherein said device is free of infectious material.

12. A pharmaceutical composition comprising the device of claim 7.

* * * * *